US007666897B2

(12) United States Patent
Jong et al.

(10) Patent No.: US 7,666,897 B2
(45) Date of Patent: Feb. 23, 2010

(54) ANALOGS OF INDOLE-3-CARBINOL METABOLITES AS CHEMOTHERAPEUTIC AND CHEMOPREVENTIVE AGENTS

(75) Inventors: Ling Jong, Sunnyvale, CA (US); Wan-Ru Chao, Sunnyvale, CA (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 12/205,532

(22) Filed: Sep. 5, 2008

(65) Prior Publication Data

US 2009/0023796 A1  Jan. 22, 2009

Related U.S. Application Data

(62) Division of application No. 11/350,232, filed on Feb. 7, 2006, now Pat. No. 7,429,610, which is a division of application No. 10/772,036, filed on Feb. 3, 2004, now Pat. No. 7,078,427, which is a division of application No. 10/224,979, filed on Aug. 20, 2002, now Pat. No. 6,800,655.

(51) Int. Cl.
*A61K 31/40* (2006.01)
*C07D 209/00* (2006.01)
(52) U.S. Cl. .................. 514/412; 548/483; 548/484
(58) Field of Classification Search ................ 514/412; 548/483, 484
See application file for complete search history.

(56) References Cited

U.S. PATENT DOCUMENTS

| | | | |
|---|---|---|---|
| 3,527,517 A | 9/1970 | Hackmann | |
| 4,636,820 A | 1/1987 | Schmidt et al. | |
| 5,086,171 A | 2/1992 | Mathiaparanam | |
| 5,116,978 A | 5/1992 | Mathiaparanam | |
| 5,206,377 A | 4/1993 | McAfee | |
| 5,266,699 A | 11/1993 | Naef et al. | |
| 5,326,879 A | 7/1994 | Takahashi et al. | |
| 5,380,723 A | 1/1995 | Takahashi et al. | |
| 5,843,607 A | 12/1998 | Hu et al. | |
| 5,942,340 A | 8/1999 | Hu et al. | |
| 5,948,808 A | 9/1999 | Safe | |
| 6,323,233 B1 | 11/2001 | Wright et al. | |
| 6,407,102 B1 | 6/2002 | Mahboobi et al. | |
| 7,048,427 B2 | 7/2006 | Jong et al. | |
| 7,429,610 B2 | 9/2008 | Jong et al. | |

FOREIGN PATENT DOCUMENTS

| | | |
|---|---|---|
| EP | 0908787 A2 | 4/1999 |
| GB | 2207670 A | 2/1989 |
| WO | WO 98/50357 | 11/1998 |
| WO | WO 99/57117 | 11/1999 |
| WO | WO 02/36561 | 5/2002 |
| WO | WO 02/36597 | 5/2002 |

OTHER PUBLICATIONS

Yudina et al., 2000, CAS: 133: 322025.*
Biswas et al., 1999, CAS: 132:122601.*
Aygün et al. (2003), "Synthesis and Biological Evaluation of Structural Variants of Carbazoquinocin C," *J. Heterocyclic Chem.* 40(3):411-417.
Biswas et al. (1998), "A Convenient Synthesis of 5,11-Dihydro-5,11-dimethyl-6-trifluoromethylindolo[3,2-b]carbazole," *Indian J. Chem. B* 37B(9):841-843.
Black et al. (1995), "Synthesis of Indolo[3,2-*b*]carbazoles from 4,6-Dimethoxyindole and Aryl Aldehydes," *Tetrahedron* 51(43):11801-11808.
Black et al. (1993), "Calix[3]indoles, New Macrocyclic Tris(indolylmethylene) Compounds with 2,7-Linkages," *J. Chem. Soc., Chem. Comm.*, 10:819-821.
Bonnesen et al. (2001), "Dietary Indoles and Isothiocyanates That Are Generated from Cruciferous Vegetables Can Both Stimulate Apoptosis and Confer Protection Against DNA Damage in Human Colon Cell Lines," *Cancer Res.* 61:6120-6130.

(Continued)

*Primary Examiner*—Rei-tsang Shiao
(74) *Attorney, Agent, or Firm*—Isaac M. Rutenberg; Mintz, Levin, Cohn, Ferris, Glovsky, and Popeo, P.C.

(57) ABSTRACT

Novel compounds useful as chemotherapeutic and chemopreventive agents are provided. The compounds are analogs of indole-3-carbinol metabolites wherein the structures and substituents of the compounds are selected to enhance the compounds' overall efficacy, particularly with respect to therapeutic activity, oral bioavailability, long-term safety, patient tolerability, and therapeutic window. The compounds are useful not only in treatment of cancer but also in prevention of cancer. One preferred class of the novel compounds has the structure of formula (IV)

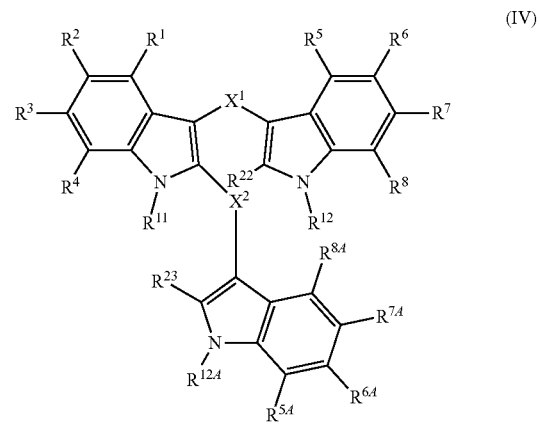

(IV)

wherein:
$R^1, R^2, R^3, R^4, R^5, R^6, R^7, R^8, R^{5A}, R^{6A}, R^{7A}, R^{8A}, R^{22}$ and $R^{23}$ are defined herein. Pharmaceutical compositions are provided as well, as are methods of synthesis and use.

25 Claims, 3 Drawing Sheets

OTHER PUBLICATIONS

Bradlow et al. (1991), "Effects of Dietary Indole-3-carbinol on Estradiol Metabolism and Spontaneous Mammary Tumors in Mice," *Carcinogenesis* 12(9):1571-1574.

Brieskorn and Huber (1979), "2,3-Bis(3-methylindolyl)methane from 3-methylindole and formaldehyde," *Archiv. Der Pharmazie* 312:1046-1051 (Abstract).

Chinni et al. (2001), "Indole-3-carbinol (I3C) Induced Cell Growth Inhibition, G1 Cell Cycle Arrest and Apoptosis in Prostate Cancer Cells," *Oncogene* 20:2927-2936.

Chu et al. (1984), A novel serotonin antagonist 2,2'-bis[3-(2-N'N-dimethylaminoethyl)indolyl]sulfide (BDIS) *J. Heterocyclic Chem.* 21:1901-1903 (Abstract).

Crowell (2005), "The chemopreventative agent development research program in the Division of Cancer Prevention of the US National Cancer Institute: An overview," *Eur. J. Cancer*, 41:1889-1910.

Fuerstner et al. (1995), "Titanium-induced zipper reactions," *Angew. Chem. Intl. Ed.* 34:678-681 (Abstract).

Grotta et al. (1961), "Preparation of Some Condensed Ring Carbazole Derivatives," *J. Org. Chem.* 26:1509-1511.

Hill and Townend (1972), "Light-induced reactions of α-(N-alkylanilino) ketones. Formation of diindolylmethanes," *J. Chem. Soc. Perkin Trans.* 9-10:1210-1219 (Abstract).

Hino et al. (1973), "Preparation of 3-Substituted 2-Indolinethiones via Diindolyl Disulfides. Reaction of 3-Substituted Indoles with Sulfur Monochloride," *Chem. Pharm. Bull.* 21(12):2739-2748 (abstract only).

Hino et al. (1974), "Reaction of Skatole with Iodine in the Presence of Thiourea," *Chem. Pharm. Bull.* 22(11): 2728-2731 (abstract only).

Hünig et al. (1976), "Synthese Vinyloger und Azavinyloger Redoxsysteme Mit Indolylresten Als Endgruppen," *Liebigs Ann. Chem.* 6:1039-1059.

Jackson et al. (1987), "Electrophilic Substitution in Indoles. Part 15. The Reaction Between Methylenedi-indoles and p-Nitrobenzenediazonium Fluoroborate," *J. Chem. Soc. Perkin Trans. I* 11:2543-2551.

Kim, and Milner (2005), "Targets for indole-3-carbinol in cancer prevention," *J. Nutritional Biochem.* 16:65-73.

Kistenmacher et al. (1992), "A Direct Synthesis of Indolocarbazoles via New Dinitroterphenyl Precursors," *J. Heterocyclic Chem.* 29:1237-1239.

Knölker et al. (1998), "Iron-Mediated Synthesis of Indolo[2,3-b]carbazole," *Tetrahedron Letters* 39:4007-4008.

Knölker et al. (2000), "Transition Metal Complexes in Organic Synthesis. Part 61: Convergent Synthesis of Indolo[2,3-b]carbazole by an Iron-Mediated Bidirectional Annulation of Two Indole Rings," *Tetrahedron* 56:4733-4737.

Kojima et al. (1994), "Chemoprevention of Spontaneous Endometrial Cancer in Female Donryu Rats by Dietary Indole-3-carbinol," *Cancer Res.* 54:1446-1449.

Lau et al. (1986), "Reductive Deoxygenation of Aryl Aldehydes and Ketones and Benzylic, Allylic, and Tertiary Alcohols by $ZnI_2$-$NaCNBH_3$," *J. Org. Chem.* 51(15):3038-3043.

Liu et al. (1994), "Indolo[3,2-b]carbazole: A Dietary-Derived Factor That Exhibits Both Antiestrogenic and Estrogenic Activity," *J. Natl. Cancer Institute* 86(23):1758-1765.

Manson et al. (2005), "Innovative agents in cancer prevention," *Recent Results Cancer Res.* 166:257-75. (Abstract).

Marshall (2003), "Cervical Dysplasia: Early Intervention," *Alternative Medicine Rev.* 8:156-170.

Michnovicz et al. (1997), "Changes in Levels of Urinary Estrogen Metabolites After Oral Indole-3-carbinol Treatment in Humans," *J. Natl. Cancer Institute* 89(10):718-723.

Napolitano et al. (1993), "Oxidation Chemistry of 5,6-Dihydroxy-2-methylindole," *Tetrahedron* 49(40):9143-9150.

Pindur et al. (1987), "Reaktivität und Reaktionswege von Methylsubstituierten Bisindolylcarbenium-Ionen," *J. Heterocyclic Chem.* 24(1):159-163.

Swindells et al. (1956), "Preparation of Indolocarbazoles. VIII. Preparation of 1-Methylindolo[2',3'—2,3]carbazole," *J. Chem. Soc.*, pp. 1135-1138.

Veronesi and Bonanni (2005), "Chemoprevention: From research to clinical oncology," *Eur. J. Cancer*, 41:1833-1841.

Von Dobeneck et al. (1969), "α,β'-Diindolylmethane und—Methene. Der Urorosein-Chromophor," *Chem. Ber.* 102(4):1347-1356.

Wille et al. (2001), "Malassezin—A Novel Agonist of the Arylhydrocarbon Receptor from the Yeast *Malassezia furfur*," *Bioorganic & Medicinal Chem.* 9:955-960.

Marzi et al., 2002, CAS:136:369712 (abstract only).
Biswas et al., 1998, CAS:130:110177 (abstract only).
Swindells et al., 1956, CAS:51:1737 (abstract only).
Fuerstner et al., 1995, CAS:123:83146 (abstract only).
Black et al., 1993, CAS: 119:271129 (abstract only).
Pindur et al., 1987, CAS: 107:217419 (abstract only).
Chu et al., 1984, CAS:102:184940 (abstract only).
Brieskorn et al., 1979, CAS:93:71451 (abstract only).
Hindo et al., 1974, CAS:82:111897 (abstract only).
Suzuki et al., 1973, CAS:80:59818 (abstract only).
Hill et al., 1972, CAS:77:5277 (abstract only).

* cited by examiner

ANALOGS OF INDOLE-3-CARBINOL METABOLITES AS CHEMOTHERAPEUTIC AND CHEMOPREVENTIVE AGENTS

CROSS-REFERENCE TO RELATED APPLICATIONS

This application is a divisional of U.S. application Ser. No. 11/350,232, filed Feb. 7, 2006, now allowed, which is a divisional of U.S. application Ser. No. 10/772,036, filed on Feb. 3, 2004, now U.S. Pat. No. 7,078,427, which is a divisional of U.S. application Ser. No. 10/224,979, filed Aug. 20, 2002, now U.S. Pat. No. 6,800,655. The aforementioned applications are incorporated by reference in their entireties.

TECHNICAL FIELD

This invention relates generally to compounds and compositions for the treatment of cancer and other hyperproliferative diseases. More particularly, the invention pertains to novel dietary indole analogs that are useful in treating a range of cancers, including estrogen-related cancers such as breast, uterine, cervical, ovarian, and endometrial cancers, and non-estrogen-related cancers such as prostate, colon, liver and lung cancers.

BACKGROUND

Cancer is the second leading cause of death in the United States, exceeded only by heart disease. Drugs that are used to treat cancer tend to be toxic at their therapeutic dose levels, commonly causing severe and even life-threatening adverse effects. Current anticancer drugs must also be administered intravenously. Consequently, nearly all cancer chemotherapy must be administered in a hospital or clinic. An additional problem with most current cancer chemotherapy is that cancers frequently develop resistance to the drugs, so that recurrence of disease is common.

For patients who have been diagnosed with cancer, cytotoxic chemotherapy is considered an essential part of the management of the disease, but resistance to chemotherapeutic drugs is unfortunately a common development in cancer. Although the mechanisms of resistance to chemotherapy are not fully understood, the cellular mechanisms thus far implicated in the development of drug resistance are the same as those that protect normal tissues from toxicity. Furthermore, the efficacy of cytotoxic chemotherapeutics is ultimately limited by their narrow therapeutic index. Therefore, it is unlikely that any breakthrough in the treatment of cancer will come about as a result of a cytotoxic approach. There is accordingly an urgent need for new noncytotoxic therapies that are safer and more effective than those currently available, and that, furthermore, will improve both survival rate and the quality of life for cancer survivors.

Recurrence is a potential threat for anyone who is diagnosed and treated with cancer, and up to 50% of patients with recurrent cancer will eventually have metastatic disease, which is often fatal. Therefore, for patients who have been treated for early stage cancer, once stabilization of the disease has been achieved, consideration must be given to adjuvant chemopreventive therapy to suppress disease for as long as possible. Since chemopreventive therapeutics are used on a long-term basis, there is a serious need for agents with three key characteristics: good tolerability, oral bioavailability, and long-term safety.

Furthermore, primary prevention is the optimal way to address any disease, and this is particularly true of cancer. Continuing advances in identification and validation of intermediate biomarkers, along with risk factors (e.g., genetic susceptibility or life-style) and exposure biomarkers, offer opportunities to more accurately assess the risk that any given individual may develop cancer. The aforementioned advances also enable a more precise identification of patient groups at an elevated risk for development of cancer, e.g., patients who may be in an otherwise undiagnosed phase of a carcinogenic process that could ultimately be fatal. Accordingly, the development of an effective cancer preventive ("chemopreventive") agent for high risk individuals is of utmost importance. Since chemopreventive agents may be given to relatively healthy subjects for extended time periods, the long-term safety of such drugs is essential.

Currently, none of the available methods for treating cancer, such as breast cancer, ovarian cancer and prostate cancer, meet all of these important criteria.

Breast cancer is one of the most prevalent types of cancer. Although breast cancer research has developed at a rapid pace over the last decade, breast cancer remains a common and devastating disease and the second leading cause of cancer-related deaths in women in the United States. Many breast tumors appear to follow a predictable clinical pattern, initially being responsive to endocrine therapy and cytotoxic chemotherapy but ultimately exhibiting a phenotype resistant to both modalities. Although the mechanisms responsible for hormone resistance of tumors remain unclear, experiments revealed that when a tumor composed of mixed populations of cells with different sensitivities to hormones was deprived of hormones, the autonomous cell types could keep growing, and inevitably the tumor growth progressed from hormone sensitive to hormone independent. Since cellular heterogeneity of estrogen receptor (ER) distribution is seen in most cases of ER-positive breast cancer, the promising treatment strategy and drugs should achieve maximal growth inhibition of both estrogen-dependent and estrogen-independent breast tumor cells at the same time.

New therapeutic agents are also needed for the treatment of ovarian cancer. Ovarian cancer has a high mortality-to-incidence ratio, is usually asymptomatic until it is diagnosed in advanced stages, and quickly develops resistance to existing chemotherapeutics. The advent of paclitaxel (Taxol) as a component of first-line and salvage therapies has further improved response rates and prolonged survival, but resistance to chemotherapeutic drugs is a common development in ovarian cancer. These chemoresistant tumor cells frequently develop a broad cross-resistance to multiple drugs, and virtually all patients in whom multiple drug resistance has developed do not survive.

With the advent of prostate-specific antigen (PSA) testing and increased public awareness, approximately 75% of prostate cancer patients now present with clinically localized disease at the time of initial diagnosis. Although detection of organ-confined disease provides the most realistic opportunity for cure, the curative potential of all presently accepted local therapies (i.e., surgery and radiation therapy) remains disappointing, while treatment-associated side effects have been shown to seriously impair sexual, urinary, and bowel function for most patients. As diagnostic modalities and screening advance, continued increases in the incidence of prostate cancer and the shift to an earlier patient age and tumor stage at diagnosis are expected in the years to come. Clearly, there is an urgent need to identify and implement novel therapeutic agents to improve cancer control while minimizing associated morbidity.

It is, therefore, of utmost importance to develop new anticancer agents that are not only effective in treating a range of cancers, but also exhibit low toxicity and have a wide therapeutic window, such that an agent allow long-term treatment to maximize disease control. An ideal anticancer agent would also be easily administrable outside of a clinical setting; orally active compounds would be particularly attractive in this regard. Ideal agents would also be useful prophylactically in patients at risk of developing cancer, or at risk of cancer recurrence, in addition to their utility in therapeutic methods.

One route to discovering safe anticancer agents is to search for dietary compounds that have anticancer properties, then to modify them to enhance their anticancer effects while retaining their safe biological profile. Known dietary compounds with anticancer activity include certain indoles, particularly indole-3-carbinol (I3C), that are found abundantly in cruciferous vegetables such as broccoli, cabbage, cauliflower, and Brussels sprouts. I3C is highly acid sensitive and it can be converted by gastric acid to form several metabolites in stomach. The four I3C metabolites shown below—3,3'-diindolyl-methane (3,3'-DIM), indolo[3,2-b]carbazole (ICZ), 2-(indol-3-ylmethyl) 3,3'-diindolyl-methane (LT), and 5,6,11,12,17,18-hexahydro-cyclonona[1,2-b:4,5-b':7,8-b"]triindole (CT)—have been identified as having antitumor activity:

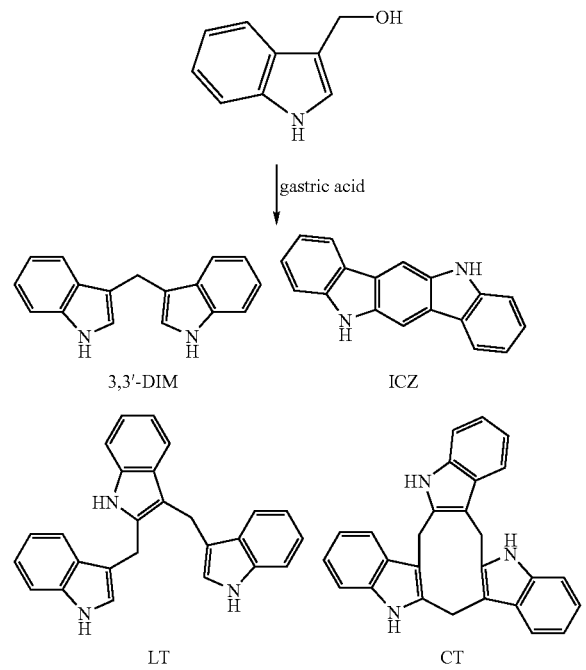

A number of in vitro and in vivo studies have shown I3C and its metabolites to have significant activity in preventing and treating estrogen-related cancers, including cancers of the breast (Bradlow et al. (1991) *Carcinogenesis* 12:1571-1574) 1991), cervix (Jin et al. (1999) *Cancer Res.* 59:3991-3997; Bell et al. (2000) *Gynecol. Oncol* 78:123-129), and endometrium (Kojima et al. (1994) *Cancer Res.* 54:1446-1449). One mechanism for this activity appears to be the antiestrogenic properties of I3C and its metabolites. These properties include P450 cytochrome-mediated induction of 2-hydroxylation of estradiol, resulting in the production of non-estrogenic metabolites (Michnovicz et al. (1990) *J. Natl. Cancer Inst.* 82:947-949; Michnovicz et al. (1997) *J. Natl. Cancer Inst.* 89:718-723). Additionally, I3C appears to directly suppress estrogen-induced signaling by the estrogen receptor in breast cancer cells (Meng et al. (2000) *J. Nutrition* 130:2927-2931).

It is known that I3C and its metabolites also possess anticancer activities that are independent of their antiestrogenic properties. For example, these compounds have been found to suppress the migration and invasion of breast cancer cells by mechanisms that include up-regulation of the BRCA1 gene, E-cadherin (a regulator of cell-cell adhesion) and PTEN (a tumor suppressor gene) (Meng et al. (2000) *J. Mol. Med.* 78:155-165). I3C and its metabolites have also been found to inhibit cell cycle progression at $G_1$ by inhibiting cyclin-dependent kinase (Cover et al. (1998) *J. Biol. Chem.* 273: 3838-3847) in both estrogen receptor-positive ($ER^+$) and estrogen receptor-negative ($ER^-$) breast cancer cells. They have also been shown to induce apoptosis in breast cancer cells by means independent of the p53 gene (Ge et al. (1999) *Anticancer Res.* 19:3199-3203), and down-regulation of the apoptosis inhibitory protein Bcl-2 (Hong et al. (2002) *Biochem. Pharmacol.* 63: 1085-1097). In addition, I3C and its metabolites appear to be protective against colon cancer by stimulating apoptosis in precancerous cells and by preventing potentially cancer-causing intracellular DNA damage (Bonnesen et al. (2001) *Cancer Res.* 61:6120-6130). I3C has also been demonstrated as useful in suppressing growth and inducing apoptosis in prostate cancer cells by mechanisms independent of its antiestrogenic properties (Chinni (2001) *Oncogene* 20:2927-2936). I3C has additionally been found to exhibit efficacy against cancers of the liver (Tanaka et al. (1990) *Carcinogenesis* 11:1403-1406) and lung (Morse et al. (1990) *Cancer Res.* 54:1446-1449). One study has found that topically administered I3C was effective in suppressing chemically induced carcinogenesis in mouse skin (Srivastava et al. (1998) *Cancer Lett.* 134:91-95). Furthermore, a clinical trial found that orally administered I3C was effective in treating the proliferative but non-cancerous disease respiratory papillomatosis (Rosen et al. (1998) *Otolaryngol. Head Neck Surg.* 118:810-815).

Results obtained by Jin et al. (1999), supra, and Chen et al. (2001) *J. Nutr.* 131(12):3294-3902, also establish I3C as having antiviral activity, insofar as I3C was found to be effective in treatment of cervical and cervical-vaginal cancers associated with human papillomavirus (HPV). Chen et al. also indicate that I3C has been found to have clinical benefits for laryngeal papillomatosis.

The present invention is the result of extensive, systematic research in the design of novel indoles in the form of structural analogs of the primary I3C metabolites that have optimized to enhance their anticancer activity and retain their safe biological profile. To the best of applicants' knowledge, the compounds and methods of the invention are completely unknown and completely unsuggested by the art.

SUMMARY OF THE INVENTION

The present invention is directed to the aforementioned need in the art, and provides novel indole analogs that are potent anticancer agents. The compounds display considerable advantages relative to existing chemotherapeutic agents. For example, the present compounds have significant anticancer activity, are effective against estrogen-dependent, estrogen-independent, drug-resistant and/or metastasized cancers, and exhibit prophylactic as well as therapeutic utility. Furthermore, many of the compounds have good oral bioavailability and have a very broad therapeutic window, in turn meaning that no toxicity will be seen even at high doses. From a safety standpoint, then, the compounds are optimal.

Furthermore, the compounds have fairly simple molecular structures, and may be readily synthesized using straightforward synthetic techniques.

The invention also provides a method for preventing or treating cancer in a mammalian individual by administration of an anticancer agent as provided herein. Generally, in chemoprevention, the patient will have been identified as being at an elevated risk of developing cancer. Such patients include, for example, those with a family history of cancer or a particular type of cancer, as well as those who have undergone genetic analysis and thereby determined to be genetically predisposed to develop cancer or a particular type of cancer. The compounds can also be used as adjuvant chemotherapeutics to prevent cancer recurrence in cancer survivors.

In a first embodiment, the aforementioned methods are carried out by administration of a therapeutically effective amount of a compound having the structure of formula (I)

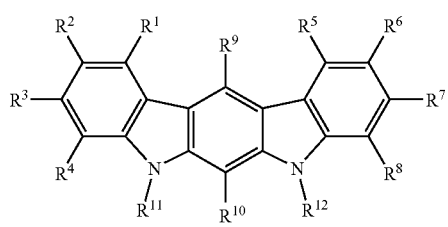

(I)

wherein:

$R^1$, $R^2$, $R^3$, $R^4$, $R^5$, $R^6$, $R^7$, $R^8$, $R^9$, and $R^{10}$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COG), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O—)$_2$), phosphinato (—P(O)(O—)), phospho (—PO$_2$), phosphino (—PH$_2$), and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and $R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl)amino-substituted $C_1$-$C_{24}$ alkyl, with the proviso that at least one of $R^1$, $R^2$, $R^3$, $R^4$, $R^5$, $R^6$, $R^7$, $R^8$, $R^9$, $R^{10}$, $R^{11}$, and $R^{12}$ is other than hydrogen.

Novel compounds within the aforementioned group are those wherein $R^1$ through $R^{12}$ are as just defined with the proviso that when $R^1$, $R^2$, $R^3$, $R^4$, $R^5$, $R^6$, $R^7$, and $R^8$ are selected from hydrogen, halo, alkyl, and alkoxy, then $R^{11}$ and $R^{12}$ are other than hydrogen and alkyl.

In another embodiment, the above-described method for treatment or prevention of cancer involves administration of a compound having the structure of formula (II)

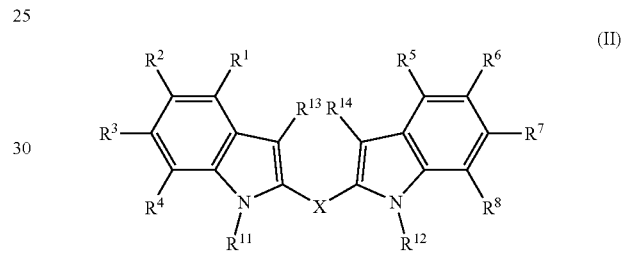

(II)

wherein:

$R^1$, $R^2$, $R^3$, $R^4$, $R^5$, $R^6$, $R^7$, and $R^8$ are independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_5$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms;

$R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl)amino-substituted $C_1$-$C_{24}$ alkyl;

$R^{13}$ and $R^{14}$ are defined as for $R^1$, $R^2$, $R^1$, $R^4$, $R^5$, $R^6$, $R^7$, and $R^8$, with the proviso that at least one of $R^{13}$ and $R^{14}$ is other than hydrogen; and X is O, S, arylene, heteroarylene, $CR^{15}R^{16}$ or $NR^{17}$ wherein $R^{15}$ and $R^{16}$ are hydrogen, $C_1$-$C_6$ alkyl, or together form $=CR^{18}R^{19}$ where $R^{18}$ and $R^{19}$ are hydrogen or $C_1$-$C_6$ alkyl, and $R^{17}$ is as defined for $R^{11}$ and $R^{12}$.

Novel compounds within the aforementioned group are those wherein only one but not both of $R^2$ and $R^6$ is amino, mono-substituted amino, or di-substituted amino.

In a still further embodiment, the above-described method for the treatment or prevention of cancer involves administration of a novel compound having the structure of formula (III)

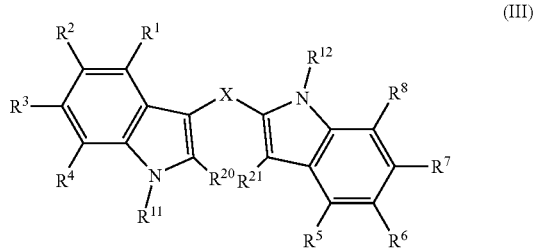

wherein:

$R^1$, $R^2$, $R^3$, $R^4$, $R^5$, $R^6$, $R^7$, $R^8$, $R^{11}$, $R^{12}$, and X are as defined for compounds having the structure of formula (II); and $R^{20}$ and $R^{21}$ are defined as for $R^1$, $R^2$, $R^3$, $R^4$, $R^5$, $R^6$, $R^7$, and $R^8$.

Additional compounds of the invention, also useful in conjunction with the above-described therapeutic and prophylactic methods, have the structure of formula (IV)

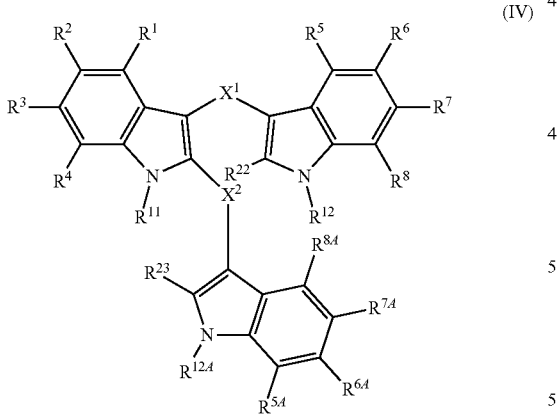

wherein:

$R^1$, $R^2$, $R^3$, $R^4$, $R^5$, $R^6$, $R^7$, $R^8$, $R^{11}$, and $R^{12}$ are defined as for compounds having the structure of formula (II);

$R^{5A}$, $R^{6A}$, $R^{7A}$, $R^{8A}$, and $R^{12A}$ are defined as for $R^5$, $R^6$, $R^7$, $R^8$, and $R^{12}$, respectively;

$R^{22}$ and $R^{23}$ are defined as for $R^{20}$ and $R^{21}$ in the structure of formula (III); and $X^1$ and $X^2$ are independently selected from O, S, arylene, heteroarylene, $CR^{15}R^{16}$ and $NR^{17}$, or together form $=CR^{18}R^{19}$ wherein $R^{15}$, $R^{16}$, $R^{17}$, $R^{18}$, and $R^{19}$ are as defined previously with respect to compounds of formulae (II), with the proviso that at least one of $R^1$, $R^2$, $R^3$, $R^4$, $R^5$, $R^6$, $R^7$, $R^8$, $R^{5A}$, $R^{6A}$, $R^{7A}$, $R^{8A}$, $R^{11}$, $R^{12}$, $R^{22}$ and $R^{23}$ is other than hydrogen.

In another embodiment, the invention encompasses pharmaceutical compositions containing a novel compound as provided herein in combination with a pharmaceutically acceptable carrier. Preferably, although not necessarily, such compositions are oral dosage forms and thus contain a carrier suitable for oral drug administration.

In still another embodiment, the invention provides methods for the prevention and treatment of various conditions, disorders and diseases that may or may not be associated with cancer. Such methods include the treatment of viral infections (including DNA viruses and retroviruses) and the treatment of estrogen-dependent disorders such as galactorrhea, McCune-Albright syndrome, benign breast disease, and endometriosis.

In a further embodiment, methods are provided for synthesizing the compounds of the invention. The methods are straightforward, avoid the use of extreme reaction conditions and toxic solvents, and provide the desired products in high yield.

DETAILED DESCRIPTION OF THE PREFERRED EMBODIMENTS

I. Definitions and Nomenclature

Figure 1:
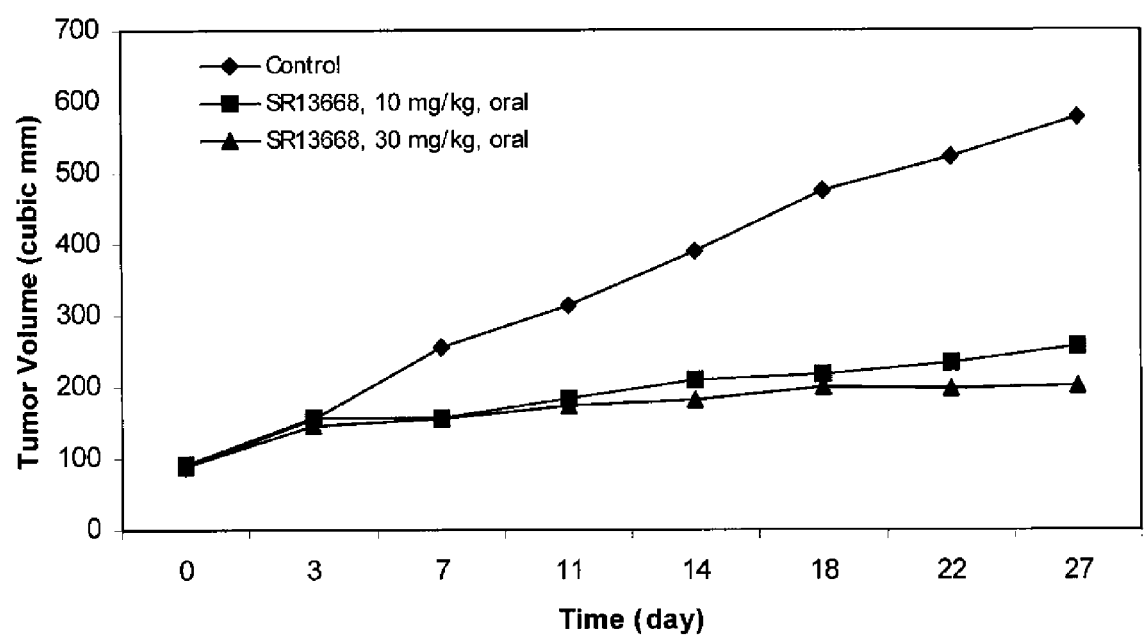
FIG. 1 is a graph illustrating the antitumorigenic activity of a compound of the invention, 2,10-dicarbethoxy-6-methoxy-5,7-dihydro-indolo[2,3-b]carbazole (compound 74), against $ER^+$ MCF-7 breast cancer xenografts in nude mice, as evaluated in Example 29.

Unless otherwise indicated, the invention is not limited to specific synthetic methods, analogs, substituents, pharmaceutical formulations, formulation components, modes of administration, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a substituent" includes a single substituent as well as two or more substituents that may be the same or different, reference to "a compound" encompasses a combination or mixture of different compounds as well as a single compound, reference to "a pharmaceutically acceptable carrier" includes two or more such carriers as well as a single carrier, and the like.

In this specification and in the claims that follow, reference will be made to a number of terms, which shall be defined to have the following meanings:

As used herein, the phrase "having the formula" or "having the structure" is not intended to be limiting and is used in the same way that the term "comprising" is commonly used.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. Preferred substituents identified as "$C_1$-$C_6$ alkyl" or "lower alkyl" contain 1 to 3 carbon atoms, and particularly preferred such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, preferably 2 to 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, preferably 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 20 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

"Hydrocarbyl" refers to univalent hydrocarbyl radicals containing 1 to about 30 carbon atoms, preferably 1 to about 24 carbon atoms, more preferably 1 to about 18 carbon atoms, most preferably about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O—)$_2$), phosphinato (—P(O)(O), phospho (—PO$_2$), and phosphino (—PH$_2$); and the hydrocarbyl moieties $C_1$-$C_{24}$ alkyl (preferably $C_1$-$C_{18}$ alkyl, more preferably $C_1$-$C_{12}$ alkyl, most preferably $C_1$-$C_6$ alkyl), $C_2$-$C_{24}$ alkenyl (preferably $C_2$-$C_{18}$ alkenyl, more preferably $C_2$-$C_{12}$ alkenyl, most preferably $C_2$-$C_6$ alkenyl), $C_2$-$C_{24}$ alkynyl (preferably $C_2$-$C_{18}$ alkynyl, more preferably $C_2$-$C_{12}$ alkynyl, most preferably $C_2$-$C_6$ alkynyl), $C_5$-$C_{20}$ aryl (preferably $C_5$-$C_{14}$ aryl), $C_6$-$C_{24}$ alkaryl (preferably $C_6$-$C_{18}$ alkaryl), and $C_6$-$C_{24}$ aralkyl (preferably $C_6$-$C_{18}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

When referring to a compound of the invention, applicants intend the term "compound" to encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. For example, treatment of a patient by administration of an anti-cancer agent of the invention encompasses chemoprevention in a patient susceptible to developing cancer (e.g., at a higher risk, as a result of genetic predisposition, environmental factors, or the like) and/or in cancer survivors at risk of cancer recurrence, as well as treatment of a cancer patient dual by inhibiting or causing regression of a disorder or disease.

By the terms "effective amount" and "therapeutically effective amount" of a compound of the invention is meant a nontoxic but sufficient amount of the drug or agent to provide the desired effect.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

II. Indole Analogs of the Invention and Synthesis Thereof

The compounds of the invention are indole analogs, more particularly, analogs of various I3C metabolites. In a first embodiment, the compounds have the structure of formula (I)

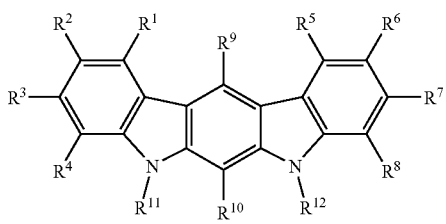

wherein:

$R^1, R^2, R^3, R^4, R^5, R^6, R^7, R^8, R^9$, and $R^{10}$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and $R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl)amino-substituted $C_1$-$C_{24}$ alkyl, with the provisos that: at least one of $R^1, R^2, R^3, R^4, R^5, R^7, R^8, R^9, R^{10}, R^{11}$, and $R^{12}$ is other than hydrogen; and when $R^1, R^2, R^3, R^4, R^5, R^6, R^7$, and $R^8$ are selected from hydrogen, halo, alkyl and alkoxy, then $R^{11}$ and $R^{12}$ are other than hydrogen and alkyl.

In preferred compounds of formula (I), $R^1, R^3, R^4, R^5, R^7, R^8$, and $R^9$ are hydrogen. These compounds have the structure of formula (Ia)

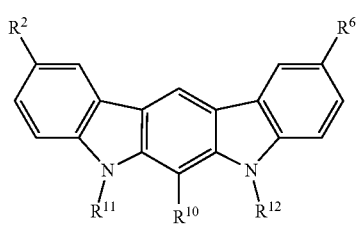

wherein $R^2, R^6, R^{10}, R^{11}$, and $R^{12}$ are as defined above, with the provisos that at least one of $R^2, R^6, R^{10}, R^{11}$, and $R^{12}$ is other than hydrogen, and that when $R^2$ and $R^6$ are selected from hydrogen, halo, alkyl, and alkoxy, then $R^{11}$ and $R^{12}$ are other than hydrogen and alkyl.

Preferred $R^2$ and $R^6$ moieties in formulae (I) and (Ia) include, without limitation, hydrogen, halo, hydroxyl, sulfhydryl, $C_1$-$C_{12}$ alkyl, $C_2$-$C_{12}$ alkenyl, $C_1$-$C_{12}$ alkoxy, $C_5$-$C_{20}$ aryloxy, $C_2$-$C_{12}$ alkylcarbonyl, $C_6$-$C_{20}$ arylcarbonyl, $C_2$-$C_{12}$ acyloxy, $C_2$-$C_{12}$ alkoxycarbonyl, $C_6$-$C_{20}$ aryloxycarbonyl, $C_2$-$C_{12}$ alkylcarbonato, carboxy, carbamoyl, mono-substituted $C_1$-$C_{12}$ alkyl-carbamoyl, di-($C_1$-$C_{12}$ alkyl)-substituted carbamoyl, amino, mono- and di-($C_1$-$C_{12}$ alkyl)-substituted amino, $C_2$-$C_{12}$ alkylamido, $C_1$-$C_{12}$ alkylsulfanyl, $C_1$-$C_{12}$ alkylsulfinyl, and $C_1$-$C_{12}$ alkylsulfonyl, including substituted analogs thereof for those substituents that permit substitution (e.g., hydroxyalkyl, aminoalkyl, dialkylaminoalkyl, aminoalkylcarbonyl, dialkylaminocarbonyl, carboxy-substituted alkyl, etc.). More preferred $R^2$ and $R^6$ moieties are halo, $C_1$-$C_{12}$ alkyl, $C_1$-$C_{12}$ alkoxy, $C_2$-$C_{12}$ alkoxycarbonyl, $C_2$-$C_{12}$ alkylcarbonato, carbamoyl, mono-substituted $C_1$-$C_{12}$ alkyl-carbamoyl, di-($C_1$-$C_{12}$ alkyl)-substituted carbamoyl, $C_1$-$C_{12}$ alkylsulfanyl, $C_1$-$C_{12}$ alkylsulfinyl, and $C_1$-$C_{12}$ alkylsulfonyl.

The $R^{10}$ substituent in structures (I) and (Ia) is preferably $C_1$-$C_{12}$ alkyl, $C_1$-$C_{12}$ haloalkyl (e.g., fluorinated alkyl, including perfluorinated alkyl), $C_1$-$C_{12}$ alkoxy, $C_1$-$C_{12}$ alkylsulfanyl, $C_2$-$C_{12}$ alkoxycarbonyl, or $C_2$-$C_{12}$ alkylcarbonato.

Preferred $R^{11}$ and $R^{12}$ moieties in structures (1) and (Ia) include, by way of example, hydrogen, $C_1$-$C_{12}$ alkyl, $C_2$-$C_{12}$ alkoxycarbonyl, amino-substituted $C_1$-$C_{12}$ alkyl, ($C_1$-$C_{12}$ alkylamino substituted $C_1$-$C_{12}$ alkyl, and di-($C_1$-$C_{12}$ alkyl) amino-substituted $C_1$-$C_{12}$ alkyl.

Those compounds of formulae (I) and (Ia) that are substituted with at least one $C_2$-$C_{12}$, preferably $C_2$-$C_6$, alkoxycarbonyl group, and/or with at least one $C_2$-$C_{12}$, preferably $C_2$-$C_6$ alkylcarbonato group, at $R^2, R^6, R^{10}, R^{11}$ and/or $R^{12}$, are particularly advantageous.

In particularly preferred compounds of formula (Ia), $R^2$ and $R^6$ are independently selected from hydrogen and $C_2$-$C_6$ alkoxycarbonyl, $R^{10}$ is halo, $C_1$-$C_6$ alkyl, $C_1$-$C_6$ haloalkyl, $C_1$-$C_6$ alkoxy, $C_1$-$C_6$ alkylsulfanyl, $C_2$-$C_6$ alkoxycarbonyl, or $C_2$-$C_6$ alkylcarbonato, and $R^{11}$ and $R^{12}$ are independently selected from hydrogen, $C_1$-$C_6$ alkoxycarbonyl and $C_1$-$C_6$ alkyl. Optimally, $R^2$ and $R^6$ are hydrogen or ethoxycarbonyl (—(CO)—O—$CH_2CH_3$), $R^{10}$ is hydrogen, methoxy, ethoxycarbonyl, ethylcarbonato (—O—(CO)—O—$CH_2CH_3$), or perfluorinated $C_1$-$C_6$ alkyl, and $R^{11}$ and $R^{12}$ are hydrogen.

Specific compounds encompassed by formula (I) include, without limitation:

5-Carbethoxy-6-ethoxycarbonyloxy-7H-indolo[2,3-b]carbazole (57);

6-Ethoxycarbonyloxy-5,7-dihydro-indolo[2,3-b]carbazole (53);

6-Methyl-5,7-dihydro-indolo[2,3-b]carbazole (60);

2,10-Dicarbethoxy-6-ethoxycarbonyloxy-5,7-dihydro-indolo[2,3-b]carbazole (63);

2,10-Dibromo-6-ethoxycarbonyloxy-5,7-dihydro-indolo[2,3-b]carbazole (64);

2,10-Dicarbethoxy-6-methyl-5,7-dihydro-indolo[2,3-b]carbazole (67);

2,10-Dicarbethoxy-6-(heptafluoropropyl)-5,7-dihydro-indolo[2,3-b]carbazole (70);

2,10-Dicarbethoxy-6-methoxy-5,7-dihydro-indolo[2,3-b]carbazole (74);

2,10-Dicarbethoxy-6-ethoxy-5,7-dihydro-indolo[2,3-b]carbazole;

2,10-Dicarbethoxy-6-(trifluoromethyl)-5,7-dihydro-indolo[2,3-b]carbazole;

2,10-Dicarbethoxy-6-(pentafluoroethyl)-5,7-dihydro-indolo[2,3-b]carbazole;
2,10-Dicarbethoxy-6-(n-propyl)-5,7-dihydro-indolo[2,3-b]carbazole;
2,10-Dicarbethoxy-6-(1,1,1-trifluoroethyl)-5,7-dihydro-indolo[2,3-b]carbazole;
2,6,10-tricarbethoxy-5,7-dihydro-indolo[2,3-b]carbazole;
2,10-Dicarbethoxy-6-ethoxycarbonyloxy-5,7-dimethyl-5,7-dihydro-indolo[2,3-b]carbazole;
6-Methoxy-5,7-dihydro-indolo[2,3-b]carbazole;
6-Ethoxy-5,7-dihydro-indolo[2,3-b]carbazole;
6-Methyl-5,7-dihydro-indolo[2,3-b]carbazole;
6-(Trifluoromethyl)-5,7-dihydro-indolo[2,3-b]carbazole;
6-(Pentafluoroethyl)-5,7-dihydro-indolo[2,3-b]carbazole;
6-(n-Propyl)-5,7-dihydro-indolo[2,3-b]carbazole;
5,7-Dimethyl-5,7-dihydro-indolo[2,3-b]carbazole-6-carboxylic acid ethyl ester;
6-Ethoxycarbonyloxy-5,7-dimethyl-5,7-dihydro-indolo[2,3-b]carbazole;
[2-(5,7-Dihydro-indolo[2,3-b]carbazol-6-yloxy)-ethyl]-dimethyl-amine;
6-(2-Dimethylamino-ethoxy)-5,7-dihydro-indolo[2,3-b]carbazole;
2,10-Dicarbethoxy-6-(2-Dimethylamino-ethoxy)-5,7-bis-(2-dimethylamino-ethyl)-5,7-dihydro-indolo[2,3-b]-carbazole;
2,10-Dibromo-5,7-dimethyl-5,7-dihydro-indolo[2,3-b]carbazole-6-carboxylic acid ethyl ester;
2,10-Dibromo-5,7-dihydro-indolo[2,3-b]carbazole-6-carboxylic acid ethyl ester;
Carbonic acid 2,10-dibromo-5,7-dihydro-indolo[2,3-b]carbazol-6-yl ester ethyl ester;
Carbonic acid 2,10-bis-dimethylcarbamoyl-5,7-dihydro-indolo[2,3-b]carbazol-6-yl ester ethyl ester;
6-Methoxy-5,7-dihydro-indolo[2,3-b]carbazole-2,10-dicarboxylic acid bis-dimethylamide;
5,7-Dihydro-indolo[2,3-b]carbazole-2,10-dicarboxylic acid bis-dimethylamide;
2,10-Bis-methanesulfinyl-5,7-dihydro-indolo[2,3-b]carbazole;
2,10-Bis-methylsulfanyl-5,7-dihydro-indolo[2,3-b]carbazole; and
2,10-Bis-methanesulfonyl-5,7-dihydro-indolo[2,3-b]carbazole.

Other novel compounds of the invention have the structure of formula (II)

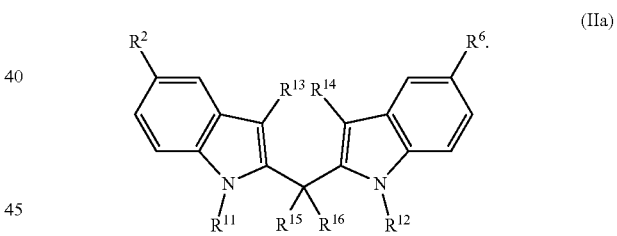

wherein:

$R^1$, $R^2$, $R^3$, $R^4$, $R^5$, $R^6$, $R^7$, and $R^8$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_5$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms, with the proviso that one but not both of $R^2$ and $R^6$ is amino, mono-substituted amino, or di-substituted amino;

$R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl)amino-substituted $C_1$-$C_{24}$ alkyl;

$R^{13}$ and $R^{14}$ are defined as for $R^1$, $R^2$, $R^3$, $R^4$, $R^5$, $R^6$, $R^7$, and $R^8$, with the proviso that at least one of $R^{13}$ and $R^{14}$ is other than hydrogen; and X is O, S, arylene, heteroarylene, $CR^{15}R^{16}$ or $NR^{17}$ wherein $R^{15}$ and $R^{16}$ are hydrogen, $C_1$-$C_6$ alkyl, or together form $=CR^{18}R^{19}$ where $R^{18}$ and $R^{19}$ are hydrogen or $C_1$-$C_6$ alkyl, and $R^{17}$ is as defined for $R^{11}$ and $R^{12}$.

In preferred compounds of formula (II), $R^1$, $R^3$, $R^4$, $R^5$, $R^7$, and $R^8$ are hydrogen, and X is $CR^{15}R^{16}$, such that the compounds have the structure of formula (IIa)

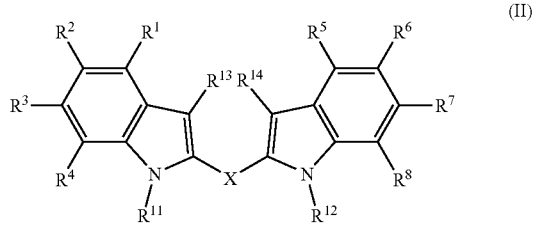

As with the compounds of formula (I) and formula (Ia), preferred $R^2$ and $R^6$ moieties in structures (II) and (IIa) include, without limitation, hydrogen, halo, hydroxyl, sulfhydryl, $C_1$-$C_{12}$ alkyl, $C_2$-$C_{12}$ alkenyl, $C_1$-$C_{12}$ alkoxy, $C_5$-$C_{20}$ aryloxy, $C_2$-$C_{12}$ alkylcarbonyl, $C_6$-$C_{20}$ arylcarbonyl, $C_2$-$C_{12}$ acyloxy, $C_2$-$C_{12}$ alkoxycarbonyl, $C_6$-$C_{20}$ aryloxycarbonyl, $C_2$-$C_{12}$ alkylcarbonato, carboxy, carbamoyl, mono-($C_1$-$C_{12}$ alkyl)-substituted carbamoyl, di-($C_1$-$C_{12}$ alkyl)-substituted carbamoyl, amino, mono- and di-($C_1$-$C_{12}$ alkyl)-substituted amino, $C_2$-$C_{12}$ alkylamido, $C_1$-$C_{12}$ alkylsulfanyl, $C_1$-$C_{12}$ alkylsulfinyl, and $C_1$-$C_{12}$ alkylsulfonyl, including substituted analogs thereof for those substituents that permit substitution (e.g., hydroxyalkyl, aminoalkyl, dialkylaminoalkyl, aminoalkylcarbonyl, dialkylaminocarbonyl, carboxy-substituted alkyl, etc.). Within the aforementioned substituents, preferred $R^2$ and $R^6$ moieties are halo, $C_1$-$C_{12}$ alkyl, $C_1$-$C_{12}$ alkoxy, $C_2$-$C_{12}$ alkoxycarbonyl, $C_2$-$C_{12}$ alkylcarbonato, carbamoyl, mono-($C_1$-$C_{12}$ alkyl)-substituted carbamoyl, di-($C_1$-$C_{12}$ alkyl)-substituted carbamoyl, $C_1$-$C_{12}$ alkylsulfanyl, $C_1$-$C_{12}$ alkylsulfinyl, and $C_1$-$C_{12}$ alkylsulfonyl. Preferred $R^{11}$ and $R^{12}$ moieties are also as given for compounds of formula (I), and thus include hydrogen, $C_1$-$C_{12}$ alkyl, $C_2$-$C_{12}$ alkoxycarbonyl, amino-substituted $C_1$-$C_{12}$ alkyl, ($C_1$-$C_{12}$ alkylamino)-substituted $C_1$-$C_{12}$ alkyl, and di-($C_1$-$C_{12}$ alkyl)amino-substituted $C_1$-$C_{12}$ alkyl.

Preferred $R^{13}$ and $R^{14}$ substituents in structures (II) and (IIa) are selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, di-($C_1$-$C_{24}$ alkyl)amino)-substituted $C_1$-$C_{24}$ alkyl, $C_5$-$C_{20}$ aryl, $C_6$-$C_{24}$ alkaryl, and $C_6$-$C_{24}$ aralkyl, and more preferred $R^{13}$ and $R^{14}$ substituents in structures (II) and (IIa) include hydrogen, $C_1$-$C_{12}$ alkyl, $C_1$-$C_{12}$ alkoxy, and $C_2$-$C_{12}$ alkoxycarbonyl.

Preferred $R^{15}$ and $R^{16}$ substituents in structure (IIa) include hydrogen and $C_1$-$C_{12}$ alkyl, and wherein $R^{15}$ and $R^{16}$ together form $=CR^{18}R^{19}$ where $R^{18}$ and $R^{19}$ are hydrogen or $C_1$-$C_6$ alkyl.

In particularly preferred compounds of formula (IIa), $R^2$ and $R^6$ are hydrogen or $C_2$-$C_6$ alkoxycarbonyl, $R^{11}$ and $R^{12}$ are hydrogen, $C_2$-$C_6$ alkoxycarbonyl, or $C_1$-$C_6$ alkyl, $R^{13}$ and $R^{14}$ are hydrogen, $C_1$-$C_6$ alkyl, $C_1$-$C_6$ alkoxy, or $C_2$-$C_6$ alkoxycarbonyl, and $R^{15}$ and $R^{16}$ are hydrogen, $C_1$-$C_6$ alkyl, or together form $=CH_2$. Optimally, $R^2$ and $R^6$ are hydrogen or ethoxycarbonyl (—(CO)—O—$CH_2CH_3$), $R^{11}$ and $R^{12}$ are hydrogen, $R^{13}$ and $R^{14}$ are independently hydrogen, methyl, or ethoxycarbonyl, and $R^{15}$ and $R^{16}$ are hydrogen or $C_1$-$C_6$ alkyl.

Exemplary compounds encompassed by formula (II) include, without limitation:

3-Methylthio-2,2'-diindolylmethane (34);
3,3'-Dimethyl-2,2'-diindolylmethane (44);
3,3'-Dimethyl-5,5'-dicarbethoxy-2,2'-diindolylmethane (46);
3,3'-Dimethyl-5-carbethoxy-2,2'-diindolylmethane
5,5'-Dicarbethoxy-2,2'-diindolylmethane;
N,N'-Dimethyl-3,3'-dimethyl-2,2'-diindolylmethane;
N,N'-Dimethyl-3,3'-dimethyl-5,5'-dicarbethoxy-2,2'-diindolylmethane;
N-Methyl-3,3'-dimethyl-5,5'-dicarbethoxy-2,2'-diindolylmethane;
N,N'-Dicarbethoxy-3,3'-dimethyl-5,5'-dicarbethoxy-2,2'-diindolylmethane; and
N-Carbethoxy-3,3'-dimethyl-5,5'-dicarbethoxy-2,2'-diindolylmethane.

In a further embodiment, compounds are provided having the structure of formula (III)

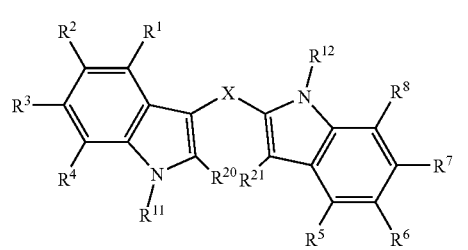

(III)

wherein:
$R^1$, $R^2$, $R^1$, $R^4$, $R^5$, $R^6$, $R^7$, $R^8$, $R^{11}$, $R^{12}$, and X are defined as for compounds of formula (II); and
$R^{20}$ and $R^{21}$ are defined as for $R^1$, $R^2$, $R^3$, $R^4$, $R^5$, $R^6$, $R^7$, and $R^8$.

In preferred compounds of formula (III), $R^1$, $R^3$, $R^4$, $R^5$, $R^7$, and $R^8$ are hydrogen, and X is $CR^{15}R^{16}$, such that the compounds have the structure of formula (IIIa)

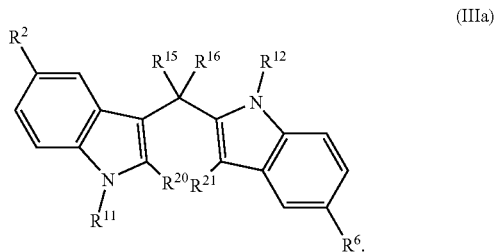

(IIIa)

Preferred $R^2$ and $R^6$ moieties in structures (III) and (IIIa) include, without limitation, hydrogen, halo, hydroxyl, sulfhydryl, $C_1$-$C_{12}$ alkyl, $C_2$-$C_{12}$ alkenyl, $C_1$-$C_{12}$ alkoxy, $C_5$-$C_{20}$ aryloxy, $C_2$-$C_{12}$ alkylcarbonyl, $C_6$-$C_{20}$ arylcarbonyl, $C_2$-$C_{12}$ acyloxy, $C_2$-$C_{12}$ alkoxycarbonyl, $C_6$-$C_{20}$ aryloxycarbonyl, $C_2$-$C_{12}$ alkylcarbonato, carboxy, carbamoyl, mono-($C_1$-$C_{12}$ alkyl)-substituted carbamoyl, di-($C_1$-$C_{12}$ alkyl)-substituted carbamoyl, amino, mono- and di-($C_1$-$C_{12}$ alkyl)-substituted amino, $C_2$-$C_{12}$ alkylamido, $C_1$-$C_{12}$ alkylsulfanyl, $C_1$-$C_{12}$ alkylsulfinyl, and $C_1$-$C_{12}$ alkylsulfonyl, including substituted analogs thereof for those substituents that permit substitution. Within the aforementioned substituents, more preferred $R^2$ and $R^6$ moieties are halo, $C_1$-$C_{12}$ alkyl, $C_1$-$C_{12}$ alkoxy, $C_2$-$C_{12}$ alkoxycarbonyl, $C_2$-$C_{12}$ alkylcarbonato, carbamoyl, mono ($C_1$-$C_{12}$ alkyl)-substituted carbamoyl, di-($C_1$-$C_{12}$ alkyl)-substituted carbamoyl, $C_1$-$C_{12}$ alkylsulfanyl, $C_1$-$C_{12}$ alkylsulfinyl, and $C_1$-$C_{12}$ alkylsulfonyl. Preferred $R^{11}$ and $R^{12}$ moieties are as given for compounds of formulae (I) and (II), and thus include hydrogen, $C_1$-$C_{12}$ alkyl, $C_2$-$C_{12}$ alkoxycarbonyl, amino-substituted $C_1$-$C_{12}$ alkyl, ($C_1$-$C_{12}$ alkylamino)-substituted $C_1$-$C_{12}$ alkyl, and di-($C_1$-$C_{12}$ alkyl)amino-substituted $C_1$-$C_{12}$ alkyl.

Preferred $R^{15}$ and $R^{16}$ substituents in structure (III) include hydrogen and $C_1$-$C_{12}$ alkyl, or wherein $R^{15}$ and $R^{16}$ together form $=CR^{18}R^{19}$ where $R^{18}$ and $R^{19}$ are hydrogen or $C_1$-$C_6$ alkyl.

Preferred $R^{20}$ and $R^{21}$ substituents in structures (III) and (IIIa) are selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, di-($C_1$-$C_{24}$ alkyl)amino)substituted $C_1$-$C_{24}$ alkyl, $C_5$-$C_{20}$ aryl, $C_6$-$C_{24}$ alkaryl, and $C_6$-$C_{24}$ aralkyl, and more preferred $R^{20}$ and $R^{21}$ substituents in structures (III) and (IIIa) include hydrogen, $C_1$-$C_{12}$ alkyl, $C_1$-$C_{12}$ alkoxy, and $C_2$-$C_{12}$ alkoxycarbonyl.

In particularly preferred compounds of formula (II), $R^2$ and $R^6$ are independently hydrogen or $C_2$-$C_6$ alkoxycarbonyl, $R^{11}$ and $R^{12}$ are independently hydrogen, $C_2$-$C_6$ alkoxycarbonyl, or $C_1$-$C_6$ alkyl, $R^{20}$ and $R^{21}$ are independently hydrogen, $C_1$-$C_6$ alkyl, $C_1$-$C_6$ alkoxy, or $C_2$-$C_6$ alkoxycarbonyl, and $R^5$ and $R^{16}$ are independently hydrogen, $C_1$-$C_6$ alkyl, or together form $=CH_2$. Optimal $R^2$ and $R^6$ substituents are hydrogen and ethoxycarbonyl (—(CO)—O—$CH_2CH_3$), optimal $R^{11}$ and $R^{12}$ substituents are hydrogen and $C_1$-$C_6$ alkyl, optimal $R^{20}$ and $R^{21}$ substituents are hydrogen, methyl, and ethoxycarbonyl, and optimal $R^{15}$ and $R^{16}$ substituents are hydrogen and $C_1$-$C_6$ alkyl.

Exemplary compounds encompassed by formula ($R^1$) include, without limitation:

2,3'-Diindolylmethane (33);
2,3'-Dimethyl-5,5'-dicarbethoxy-2',3-diindolylmethane (53);
2,3'-Dimethyl-2',3-diindolylmethane;
5,5'-Dicarbethoxy-2',3-diindolylmethane;
5-Carbethoxy-2,3'-dimethyl-2',3-diindolylmethane;
N,N'-Dimethyl-2,3'-diindolylmethane;
N,N'-Dimethyl-2,3'-dimethyl-2',3-diindolylmethane;
N,N'-Dimethyl-2,3'-Dimethyl-5,5'-dicarbethoxy-2',3-diindolylmethane;
N-Methyl-2,3'-Dimethyl-5,5'-dicarbethoxy-2',3-diindolylmethane;
N,N'-Dicarbethoxy-2,3'-Dimethyl-5,5'-dicarbethoxy-2',3-diindolylmethane; and
N-Carbethoxy-2,3'-Dimethyl-5,5'-dicarbethoxy-2',3-diindolylmethane.

Additional compounds of the invention have the structure of formula (IV)

(IV)

wherein:

$R^1$, $R^2$, $R^3$, $R^4$, $R^5$, $R^6$, $R^7$, $R^8$, $R^{11}$, and $R^{12}$ are defined as for compounds having the structure of formula (II);

$R^{5A}$, $R^{6A}$, $R^{7A}$, $R^{8A}$, and $R^{12A}$ are defined as for $R^5$, $R^6$, $R^7$, $R^8$, and $R^{12}$, respectively;

$R^{22}$ and $R^{23}$ are defined as for $R^{20}$ and $R^{21}$ in the structure of formula (III); and $X^1$ and $X^2$ are independently selected from O, S, arylene, heteroarylene, $CR^{15}R^{16}$, and $NR^{17}$ wherein $R^{15}$ and $R^{16}$ are hydrogen, $C_1$-$C_6$ alkyl, or together form =$CR^{18}R^{19}$ where $R^{18}$ and $R^{19}$ are hydrogen or $C_1$-$C_6$ alkyl, and $R^{17}$ is as defined for $R^{11}$ and $R^{12}$, with the proviso that at least one of $R^1$, $R^2$, $R^3$, $R^4$, $R^5$, $R^6$, $R^7$, $R^8$, $R^{5A}$, $R^{6A}$, $R^{7A}$, $R^{8A}$, $R^{11}$, $R^{12}$, $R^{22}$ and $R^{23}$ is other than hydrogen.

In preferred compounds of formula (IV), $R^1$, $R^3$, $R^4$, $R^5$, $R^7$, $R^8$, $R^{5A}$, $R^{7A}$, and $R^{8A}$ are hydrogen, and $X^1$ and $X^2$ are $CH_2$, such that the compounds have the structure of formula (IVa)

(IVa)

with the proviso that at least one of $R^2$, $R^6$, $R^{6A}$, $R^{11}$, $R^{12}$, $R^{12A}$, $R^{22}$ and $R^{23}$ is other than hydrogen.

Preferred $R^2$, $R^6$, and $R^{6A}$ moieties in structures (IVa) include, without limitation, hydrogen, halo, hydroxyl, sulfhydryl, $C_1$-$C_{12}$ alkyl, $C_2$-$C_{12}$ alkenyl, $C_1$-$C_{12}$ alkoxy, $C_5$-$C_{20}$ aryloxy, $C_2$-$C_{12}$ alkylcarbonyl, $C_6$-$C_{20}$ arylcarbonyl, $C_2$-$C_{12}$ acyloxy, $C_2$-$C_{12}$ alkoxycarbonyl, $C_6$-$C_{20}$ aryloxycarbonyl, $C_2$-$C_{12}$ alkylcarbonato, carboxy, carbamoyl, mono-($C_1$-$C_{12}$ alkyl)-substituted carbamoyl, di-($C_1$-$C_{12}$ alkyl)-substituted carbamoyl, amino, mono- and di-($C_1$-$C_{12}$ alkyl)-substituted amino, $C_2$-$C_{12}$ alkylamido, $C_1$-$C_{12}$ alkylsulfanyl, $C_1$-$C_{12}$ alkylsulfinyl, and $C_1$-$C_{12}$ alkylsulfonyl, including substituted analogs thereof for those substituents that permit substitution. Within the aforementioned substituents, preferred $R^2$, $R^6$, and $R^{6A}$ moieties are halo, $C_1$-$C_{12}$ alkyl, $C_1$-$C_{12}$ alkoxy, $C_2$-$C_{12}$ alkoxycarbonyl, $C_2$-$C_{12}$ alkylcarbonato, carbamoyl, mono-($C_1$-$C_{12}$ alkyl)-substituted carbamoyl, di-($C_1$-$C_{12}$ alkyl)-substituted carbamoyl, $C_1$-$C_{12}$ alkylsulfanyl, $C_1$-$C_{12}$ alkylsulfinyl, and $C_1$-$C_{12}$ alkylsulfonyl. In more preferred compounds, at least one of $R^2$, $R^6$, and $R^{6A}$ is $C_2$-$C_{12}$ alkoxycarbonyl or $C_2$-$C_{12}$ alkylcarbonato. Preferred $R^{11}$, $R^{12}$, and $R^{12A}$ moieties include, without limitation, hydrogen, $C_1$-$C_{12}$ alkyl, $C_2$-$C_{12}$ alkoxycarbonyl, amino-substituted $C_1$-$C_{12}$ alkyl, ($C_1$-$C_{12}$ alkylamino)-substituted $C_1$-$C_{12}$ alkyl, and di-($C_1$-$C_{12}$ alkyl) amino-substituted $C_1$-$C_{12}$ alkyl.

Preferred $R^{22}$ and $R^{23}$ substituents in structures (IV) and (IVa) are selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, di-($C_1$-$C_{24}$ alkyl)amino)substituted $C_1$-$C_{24}$ alkyl, $C_5$-$C_{20}$ aryl, $C_6$-$C_{24}$ alkaryl, and $C_6$-$C_{24}$ aralkyl, and more preferred $R^{22}$ and $R^{23}$ substituents in structures (II) and (IIa) include hydrogen, $C_1$-$C_{12}$ alkyl, $C_1$-$C_{12}$ alkoxy, and $C_2$-$C_{12}$ alkoxycarbonyl.

In particularly preferred compounds of formula (IVa), $R^2$, $R^6$, $R^{6A}$, $R^{22}$, and $R^{23}$ are independently hydrogen or $C_2$-$C_6$ alkoxycarbonyl, and $R^{11}$, $R^{12}$, and $R^{12A}$ are independently hydrogen, or $C_1$-$C_6$ alkyl. Optimally, $R^2$, $R^6$, $R^{6A}$, $R^{22}$, and $R^{23}$ are hydrogen or ethoxycarbonyl (—(CO)—O—$CH_2CH_3$).

Examples of specific compounds encompassed by formula (IV) include, without limitation:

2-(2-Carbethoxy-indol-3-ylmethyl)-2'-carbethoxy-3,3'-diindolylmethane (75);

2-(5-Bromo-indol-3-ylmethyl)-5,5'-dibromo-3,3'-diindolylmethane (76); and 2-(5-Carbethoxy-indol-3-ylmethyl)-5,5'-dicarbethoxy-3,3'-diindolylmethane (79).

A compound of the invention may be administered in the form of a salt, ester, amide, prodrug, active metabolite, analog, or the like, provided that the salt, ester, amide, prodrug, active metabolite or analog is pharmaceutically acceptable and pharmacologically active in the present context. Salts, esters, amides, prodrugs, active metabolites, analogs, and other derivatives of the active agents may be prepared using standard procedures known to those skilled in the art of synthetic organic chemistry and described, for example, by J. March, *Advanced Organic Chemistry: Reactions, Mechanisms and Structure,* 4th Ed. (New York: Wiley-Interscience, 1992).

For example, acid addition salts may be prepared from a free base (e.g., a compound containing a primary amino group) using conventional methodology involving reaction of the free base with an acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of any acidic moieties that may be present may be carried out in a similar manner using a pharmaceutically acceptable base such as sodium hydroxide, potassium hydroxide, ammonium hydroxide, calcium hydroxide, trimethylamine, or the like. Preparation of esters involves reaction of a hydroxyl group with an esterification reagent such as an acid chloride. Amides may be prepared from esters, using suitable amine reactants, or they may be prepared from an anhydride or an acid chloride by reaction with ammonia or a lower alkyl amine. Prodrugs, conjugates, and active metabolites may also be prepared using techniques known to those skilled in the art or described in the pertinent literature. Prodrugs and conjugates are typically prepared by covalent attachment of a moiety that results in a compound that is therapeutically inactive until modified by an individual's metabolic system.

In addition, those novel compounds containing chiral centers can be in the form of a single enantiomer or as a racemic mixture of enantiomers. In some cases, i.e., with regard to certain specific compounds illustrated herein, chirality (i.e., relative stereochemistry) is indicated. In other cases, it is not, and such structures are intended to encompass both the enantiomerically pure form of the compound shown as well as a racemic mixture of enantiomers. Preparation of compounds in enantiomerically form may be carried out using an enantioselective synthesis; alternatively, the enantiomers of a chiral compound obtained in the form of the racemate may be separated post-synthesis, using routine methodology.

Other derivatives and analogs of the active agents may be prepared using standard techniques known to those skilled in the art of synthetic organic chemistry, or may be deduced by reference to the pertinent literature.

The compounds of the invention may be readily synthesized using straightforward techniques, from appropriately substituted indoles that serve as starting materials (Moyer et al. (1986) *J. Org. Chem.* 51: 5106-5110). Indole precursors used to synthesize the compounds of the invention may be prepared using conventional techniques, such as by treatment of nitrotoluene (V)

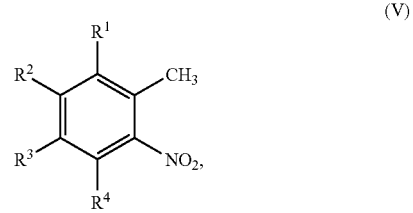

with N,N-dimethylformamide dimethyl acetal and pyrrolidine, to give the intermediate enamine (VI), which can then be cyclized by reduction with zinc in acetic acid to give the indole (VII).

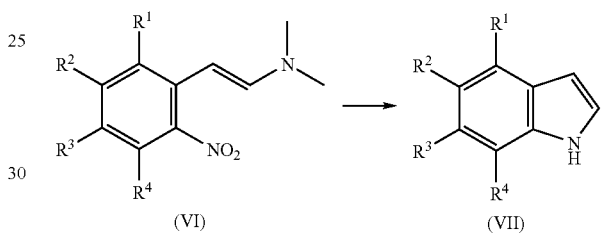

The indole precursor (VII), substituted with one or more substituents selected to result in the desired substituents on the product, is then appropriately treated to provide a reactive site capable of rendering the molecule able to self-condense. For example, precursor (VII) can be formylated (e.g., with phosphorus oxychloride and N,N-dimethylformamide) to give the aldehyde (IX), followed by reduction with a suitable reducing agent (e.g., sodium borohydride) to the 3-hydroxymethyl-indole analog (X), as follows:

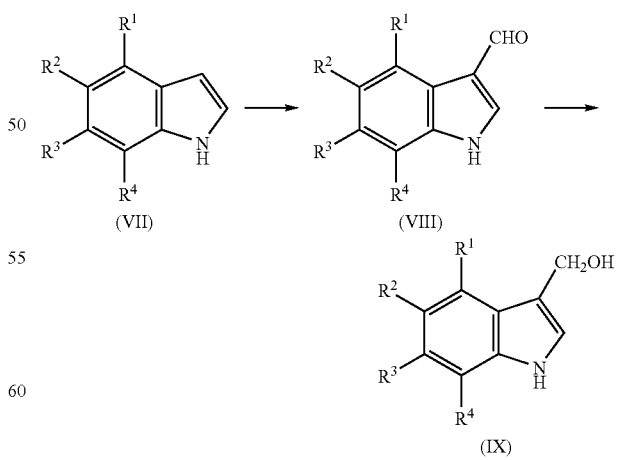

Compound (IX) will then readily self-condense under aqueous basic conditions to give the substituted 3,3'-diindolylmethane (X):

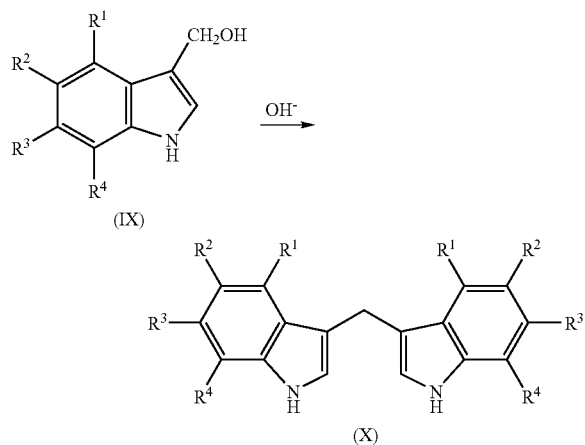

Alternatively, compound (IX) may be condensed with a differently substituted indole analog to provide the substituted 3,3'-diindolylmethane (XII):

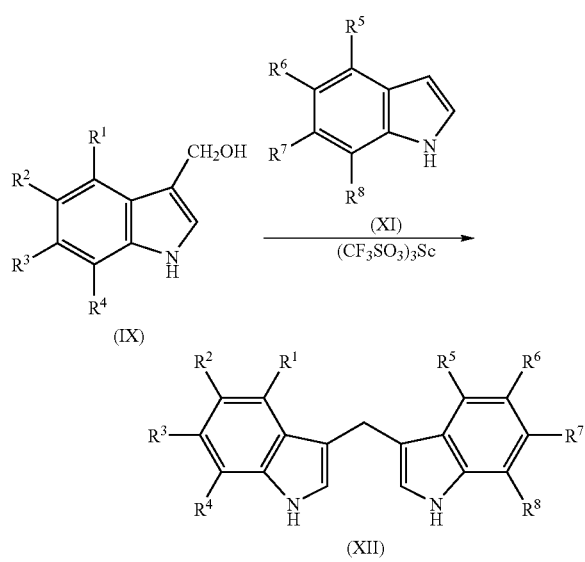

For example, the aforementioned reaction may be carried out with 5-bromo-3-hydroxymethylindole (compound (IX), wherein $R^1$, $R^3$, and $R^4$ are hydrogen and $R^2$ is bromo) and 5-bromoindole (compound (XI), wherein $R^5$, $R^7$, and $R^8$ are hydrogen and $R^6$ is bromo), to provide the 5,5'-dibromo analog of (XII). Various reactions may then be carried out to replace the bromine substituents with other moieties, for example, with:

carboxylic ester groups, introduced by reaction of a brominated indole analog (e.g., 5,5'-dibromo-3,3'-diindolylmethane) with an alkyl, aryl, or aralkyl chloroformate (e.g., ethyl chloroformate or benzylchloroformate), during which the nitrogen atoms are protected;

carboxyl groups, prepared by basic hydrolysis of the carboxylic ester groups;

alkylsulfanyl (thioalkyl) groups, prepared by reaction of a brominated indole analog (e.g., 5,5'-dibromo-3,3'-diindolylmethane) with a disulfide, e.g., methyldisulfanyl methane;

alkylsulfonyl groups, prepared by oxidation of the alkylsulfanyl groups; and amides, by reaction of a brominated indole analog (e.g., 5,5'-dibromo-3,3'-diindolylmethane) with a carbamyl halide (e.g., dimethylcarbamyl chloride).

The 3,3'-diindolylmethane analogs so prepared may then be used directly in the synthesis of compounds of formula (I), i.e., 5,7-dihydro-indolo[2,3-b]carbazoles. The reaction is carried out via cyclization of a 3,3'-diindolylmethane analog of formula (XII) by: (1) protecting the indolyl nitrogen atoms of a compound (XII) with a suitable amino protecting group, to provide an N-protected intermediate (XIII); and (2) treating the protected compound so provided with an organolithium reagent LiR, optionally in conjunction with a compound selected to provide a nonhydrogen substituent $R^{10}$:

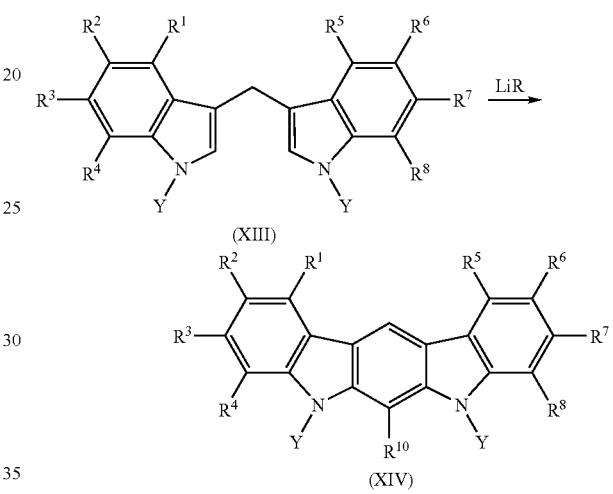

In compounds (XIII) and (XIV), Y is the amino protecting group, which may be any suitable protecting group that is inert with respect to the organolithium reagent but may be removed following synthesis of (XIV). Preferred amino protecting groups are carbamates, e.g., alkyl carbonates such as t-butyloxycarbonyl, or "BOC." Other suitable amino protecting groups will be known to those in the field of synthetic organic chemistry, and/or are described in the pertinent texts and literature. See, e.g., Greene et al., *Protective Groups in Organic Synthesis*, 3rd Ed. (New York: Wiley, 1999). The organolithium reagent LiR, as will be appreciated by those of ordinary skill in the art, may be an alkyllithium reagent such as methyl lithium, isopropyl lithium, n-butyllithium, s-butyllithium, t-butyllithium, or the like, or an aryllithium lithium reagent, e.g., phenyl lithium or p-tolyl lithium, or a lithium amide reagent, e.g., lithium 2,2,6,6-tetramethylpiperidide (LiTMP) or lithium diisopropylamide.

The optional additional reactant selected to provide a non hydrogen $R^{10}$ substituent as shown will depend, of course, on the particular $R^{10}$ substituent intended. Examples of such reactants include, without limitation, anhydrides, acyl chlorides, alkyl and aryl carbonate, and alkyl and aryl chloroformates. For example, carrying out the reaction with LiTMP and an anhydride R—(CO)—O—(CO)—R, wherein R is alkyl, substituted alkyl, aryl, etc., will result in the substituent R at the $R^{10}$ position. See Examples 20 and 21, describing preparation of 6-methyl-indolo[2,3-b]carbazole and a 6-perfluoroalkyl-substituted (i.e., 6-heptafluoropropyl-substituted) 5,7-dihydro-indolo[2,3-b]carbazole, respectively. As another example, carrying out the reaction with LiTMP and an alkyl chloroformate, such as ethyl chloroformate, will provide an alkylcarbonato, e.g., an ethylcarbonato, substituent —O—(CO)—O—CH$_2$CH$_3$ at R$^{10}$. See Example 18, describing preparation of 2,10-dicarbethoxy-6-ethoxycarbonyloxy-5,7-dihydro-indolo[2,3-b]carbazole. The procedure described therein can also generate the 6-hydroxyl and 6-alkoxy analogs, by addition of an acid, e.g., acetic acid, at low temperature (to provide the 6-hydroxyl analog), followed by alkylation using standard procedures (see Example 22).

Compounds of formula (II) herein, i.e., 2,2'-diindolylmethane analogs, are synthesized using procedures that are analogous to those described above with respect to synthesis of 3,3'-diindolylmethane analogs. However, in the synthesis of 2,2'-diindolylmethane analogs, the C3-position of the indole precursor is blocked to enable reaction at the less active (C2) site. The reaction, illustrated below with the blocking group identified as "Z," may be represented as follows:

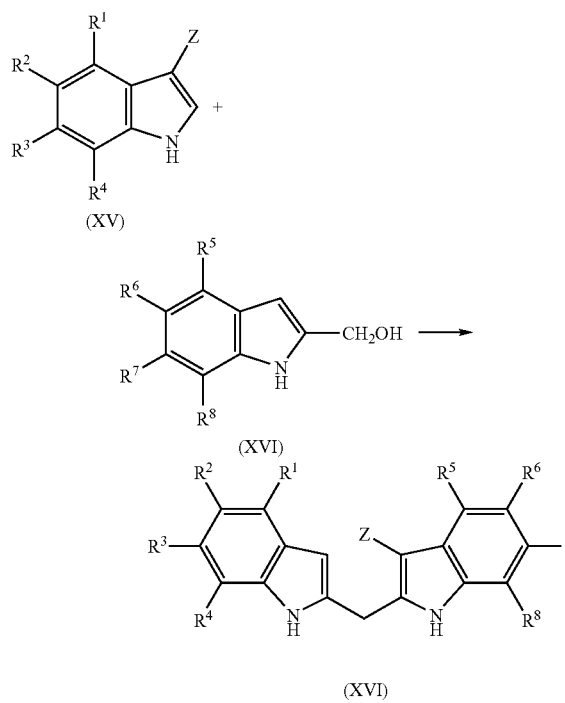

Z is preferably selected so as to be readily removable from the product (XVI); an ideal blocking group is methylthio or bromo, which can be removed by reductive elimination using a suitable catalyst.

Compounds of formula (III), i.e., 2,3'-diindolylmethane analogs, are also made by coupling two appropriately substituted indolyl precursors, the first of which has the structure of formula (IX), and the second of which has the structure of formula (XV), such that the linkage in the product is provided between the C3-position of the indole precursor (IX) and the C2-position of the C3-"blocked" indole precursor (XV). Appropriate reagents and reaction conditions are analogous to those described above with respect to synthesis of the 3,3'-diindolylmethane and 2,2'-diindolylmethane analogs. Specific procedures for preparing 2,3'-diindolylmethane analogs are described in Examples 11 and 15.

Compounds of formula (IV) may be synthesized by reaction of an indolyl precursor having the structure of formula (IX) with a second indolyl precursor that is unsubstituted at both the C2 and C3 positions, which results in reaction at both sites. Illustrative reactions are described in detail in Examples 23 and 24.

III. Pharmaceutical Formulations and Modes of Administration

The novel compounds may be conveniently formulated into pharmaceutical formulations composed of one or more of the compounds in association with a pharmaceutically acceptable carrier. See *Remington: The Science and Practice of Pharmacy*, 19$^{th}$ Ed. (Easton, Pa.: Mack Publishing Co., 1995), which discloses typical carriers and conventional methods of preparing pharmaceutical formulations.

The compounds of the invention may be administered orally, parenterally, rectally, vaginally, buccally, sublingually, nasally, by inhalation, topically, transdermally, or via an implanted reservoir in dosage forms containing conventional non-toxic pharmaceutically acceptable carriers and excipients. The term "parenteral" as used herein is intended to include subcutaneous, intravenous, and intramuscular injection. The amount of the compound administered will, of course, be dependent on the particular active agent, the condition or disorder being treated, the severity of the condition or disorder, the subjects weight, the mode of administration and other pertinent factors known to the prescribing physician. Generally, however, dosage will be in the range of approximately 0.001 mg/kg/day to 100 mg/kg/day, more preferably in the range of about 0.1 mg/kg/day to 10 mg/kg/day.

Depending on the intended mode of administration, the pharmaceutical formulation may be a solid, semi-solid or liquid, such as, for example, a tablet, a capsule, caplets, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in *Remington: The Science and Practice of Pharmacy*, cited above.

For those compounds that are orally active, oral dosage forms are generally preferred, and include tablets, capsules, caplets, solutions, suspensions and syrups, and may also comprise a plurality of granules, beads, powders or pellets that may or may not be encapsulated. Preferred oral dosage forms are tablets and capsules.

Tablets may be manufactured using standard tablet processing procedures and equipment. Direct compression and granulation techniques are preferred. In addition to the active agent, tablets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose, and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, *Remington: The Science and Practice of Pharmacy*, cited supra, which describes materials and methods for preparing encapsulated pharmaceuticals.

Oral dosage forms, whether tablets, capsules, caplets, or particulates, may, if desired, be formulated so as to provide for gradual, sustained release of the active agent over an extended time period. Generally, as will be appreciated by those of ordinary skill in the art, sustained release dosage forms are formulated by dispersing the active agent within a matrix of a gradually hydrolyzable material such as an insoluble plastic (e.g., polyvinyl chloride or polyethylene), or a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Preparations according to this invention for parenteral administration include sterile nonaqueous solutions, suspensions, and emulsions. Examples of nonaqueous solvents or vehicles are propylene glycol, polyethylene glycol, vegetable oils, such as olive oil and corn oil, gelatin, and injectable organic esters such as ethyl oleate. Parenteral formulations may also contain adjuvants such as preserving, wetting, emulsifying, and dispersing agents. The formulations are rendered sterile by incorporation of a sterilizing agent, filtration through a bacteria-retaining filter, irradiation, or heat. They can also be manufactured using a sterile injectable medium.

The compounds of the invention may also be administered through the skin or mucosal tissue using conventional transdermal drug delivery systems, wherein the active agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

Although the present compositions will generally be administered orally, parenterally, or transdermally, other modes of administration are suitable as well. For example, administration may be rectal or vaginal, preferably using a suppository that contains, in addition to the active agent, excipients such cocoa butter or a suppository wax. Formulations for nasal or sublingual administration are also prepared with standard excipients well known in the art. The pharmaceutical compositions of the invention may also be formulated for inhalation, e.g., as a solution in saline, as a dry powder, or as an aerosol.

The compounds of the invention are useful in the prevention and treatment of many different types of cancer, including estrogen-dependent, estrogen-independent, drug-resistant and/or metastasized cancers. For example, the present compounds exhibit efficacy with respect to the prevention and treatment of estrogen-dependent cancers such as cancers of the breast, cervix, uterus, ovaries, and endometrium, and additionally exhibit prophylactic as well as therapeutic utility with regard to cancers that are not estrogen-dependent, including, without limitation, cancers of the prostate, liver, lung, colon, and pancreas, including drug-resistant forms of these cancers. Efficacy against drug-resistant cancers represents an important advance in the art, as a major problem affecting the efficacy of chemotherapy regimens is the evolution of cancer cells that, upon exposure to a chemotherapeutic drug, become resistant to a multitude of structurally unrelated drugs and therapeutic agents.

Generally, in chemoprevention, the patient will have been identified as being at an elevated risk of developing cancer. Such patients include, for example, those with a family history of cancer or a particular type of cancer, as well as those who have undergone genetic analysis and thereby determined to be genetically predisposed to develop cancer or a particular type of cancer. The compounds can also be used as adjuvant chemotherapeutics to prevent cancer recurrence in cancer survivors.

The compounds of the invention are also useful in the prevention and treatment of viral infections, including DNA viruses (such as the adenovirus, papillomavirus, and herpesvirus groups) as well as retroviral infections. Specific examples of DNA viruses include hepatitis B virus, SV 40, individual human papillomavirus species and, individual equine, feline, canine, simian, murine, avian, and human herpes virus species, which include human herpesvirus 1-8 (HHV-1-HHV-8). Retroviruses include, by way of example, the human spumavirus, mouse mammary tumor virus, avian leukosis virus, murine leukemia virus, rous sarcoma virus, feline leukemia virus (FELV), feline immunodeficiency virus (FIV), simian immunodeficiency virus (SIV), hepatitis C virus, human T cell leukemia species (HTLV1, 2), IV-1, and HIV-2.

The compounds are additionally useful in the prevention and treatment of a number of estrogen-dependent disorders other than estrogen-dependent cancers. By an "estrogen-dependent disorder" is meant a condition or disease that is estrogen-induced or estrogen-stimulated. Estrogen-dependent disorders other than cancer that can be treated with the compounds of the invention include galactorrhea, McCune-Albright syndrome, benign breast disease, and endometriosis.

It is to be understood that while the invention has been described in conjunction with the preferred specific embodiments thereof, the description above as well as the examples that follow are intended to illustrate and not limit the scope of the invention. Other aspects, advantages and modifications within the scope of the invention will be apparent to those skilled in the art to which the invention pertains.

All patents, patent applications, journal articles, and other reference cited herein are incorporated by reference in their entireties.

EXPERIMENTAL $^1$H and $^{13}$C NMR spectra were recorded on a Varian Gemini 300 MHz spectrometer (300 MHz and 75 MHz, respectively) and are internally referenced to chloroform at δ 7.27. Data for $^1$H NMR are reported as follows: chemical shift (δ ppm), multiplicity (s=singlet, d=doublet, t=triplet, q=quartet, m=multiplet), coupling constant (Hz), integration, and assignment. Data for $^{13}$C are reported in terms of chemical shift. IR spectra were recorded on a Perkin-Elmer 1610 spectrometer and are reported in terms of frequency of absorption (cm$^{-1}$). Mass spectra were obtained using a ThermoFinnigan LCQ Duo LC/MS/MS instrument and an electrospray ionization probe. Thin-layer chromatography was run on Analtech Uniplate silica gel TLC plates.

Scheme 1 illustrates the reactions of Examples 1 and 2:

SCHEME I:

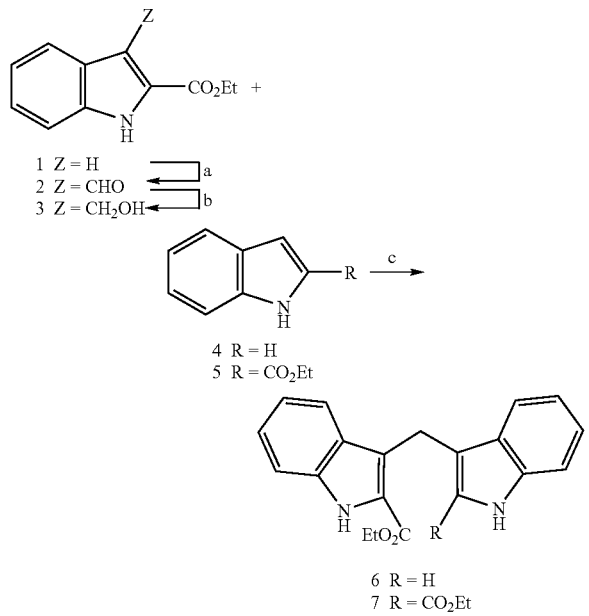

a. N-methyl formanilide, POCl$_3$, aq. CH$_3$CO$_2$Na.
b. NaBH$_4$.
c. (CF$_3$SO$_3$)$_3$Sc.

Example 1

Synthesis of 2-Carbethoxy-3,3'-diindolylmethane (6)

(a) Ethyl 3-formyl-indole-2-carboxylate (2). To a mixture of N-methyl formanilide (4.2 g, 31 mmol) and phosphorus oxychloride (POCl$_3$; 2.9 mL, 30.7 mmol) under argon was added ethylene dichloride (16 mL) and ethyl indole-2-carboxylate (1) (5.0 g, 26.4 mmol), and refluxed for 1.5 h. The reaction mixture was cooled to room temperature, poured into saturated aqueous sodium acetate (CH$_3$CO$_2$Na), and the precipitate collected by filtration, washed with H$_2$O, ether and dried under vacuum overnight to give the desired product 2 as a solid in quantitative yield (6.0 g): $^1$H NMR (300 MHz, CDCl$_3$) δ 1.48 (t, J=7.1 Hz, 3, CO$_2$CH$_2$CH$_3$), 4.54 (q, J=7.1 Hz, 2, CO$_2$CH$_2$CH$_3$), 7.36 (m, 1, ArH), 7.45 (m, 2, ArH), 8.49 (d, J=8.2 Hz, 1, ArH), 9.33 (br.s, 1, NH), 10.77 (s, 1, CHO).

(b) Ethyl 3-hydroxymethyl-indole-2-carboxylate (3). To a solution of aldehyde 2 (0.85 g, 3.9 mmol) in tetrahydrofuran (THF) (20 mL) was added sodium borohydride (NaBH$_4$) (0.2 g, 5.3 mmol) slowly at room temperature and stirred for 1 h under argon. The suspension was quenched slowly with water and the organic layer was separated, dried over magnesium sulfate, and concentrated to afford a solid 3 in quantitative yield (0.86 g): $^1$H NMR (300 MHz, CDCl$_3$) δ 1.45 (t, J=7.1 Hz, 3, CO$_2$CH$_2$CH$_3$), 4.46 (q, J=7.1 Hz, 2, CO$_2$CH$_2$CH$_3$), 5.10 (s, 2, CH$_2$OH), 7.19 (m, 1, ArH), 7.37 (m, 2, ArH), 7.78 (m, 1, ArH), 8.83 (br.s, 1, NH).

(c) 2-Carbethoxy-3,3'-diindolylmethane (6). To a mixture of ethyl 3-hydroxymethyl-indole-2-carboxylate (3) (1 g, 4.56 mmol) and indole (4) (0.6 g, 5.12 mmol) in CH$_2$Cl$_2$ (10 mL) was added (CF$_3$SO$_3$)$_3$Sc (0.2 g) and stirred for overnight under argon. The solvent was evaporated to give a crude product. Flash chromatography (20% EtOAc/hexane) yielded 6 as a white solid (0.95 g, 65%): $^1$H NMR (300 MHz, CDCl$_3$) δ 1.35 (t, J=7.1 Hz, 3, CO$_2$CH$_2$CH$_3$), 4.41 (q, J=7.1 Hz, 2, CO$_2$CH$_2$CH$_3$), 4.64 (s, 2, CH$_2$), 6.80 (m, 1, PyH), 7.06 (m, 1, ArH), 7.11 (m, 1, ArH), 7.18 (m, 1, ArH), 7.31 (m, 2, ArH), 7.38 (m, 1, ArH), 7.66 (m, 1, ArH), 7.74 (m, 1, ArH), 7.85 (br.s, 1, NH), 8.76 (br.s, 1, NH).

Example 2

Synthesis of 2,2'-Dicarbethoxy-3,3'-diindolylmethane (7)

2,2'-Dicarbethoxy-3,3'-diindolylmethane (7). To a mixture of 3-hydroxymethyl-indole-2-carboxylate (3) (0.4 g, 1.82 mmol) and ethyl indole-2-carboxylate (5) (0.42 g, 2.2 mmol) in CH$_2$Cl$_2$ (10 mL) was added (CF$_3$SO$_3$)$_3$Sc (0.09 g) and stirred for overnight under argon. The solvent was evaporated to give a crude product, which was washed with H$_2$O; ether and dried on vacuum overnight to yield the desired product 7 as a white solid (0.67 g, 94%): $^1$H NMR (300 MHz, CDCl$_3$) δ 1.42 (t, J=7.1 Hz, 6, CO$_2$CH$_2$CH$_3$), 4.48 (q, J=7.1 Hz, 4, CO$_2$CH$_2$CH$_3$), 5.15 (s, 2, CH$_2$), 6.91 (m, 2, ArH), 7.21 (m, 2, ArH), 7.33 (m, 2, ArH), 7.43 (m, 2, ArH), 8.75 (br.s, 2, NH).

Scheme II illustrates the reactions described in Examples 3 and 4:

Scheme II.

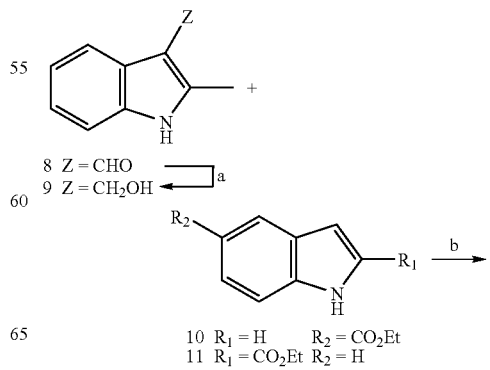

-continued

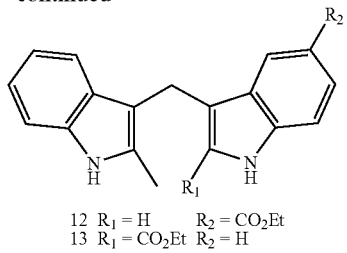

12 R₁ = H, R₂ = CO₂Et
13 R₁ = CO₂Et, R₂ = H a. NaBH₄.
b. (CF₃SO₃)₃Sc.

Example 3

Synthesis of 5-Carbethoxy-2'-methyl-3,3'-diindolyl-methane (12)

(a) 2-Methylindole-3-carbinol (9). To a solution of aldehyde 8 (2 g, 12.56 mmol) in wet THF (30 mL) was added NaBH₄ (0.71 g, 18.8 mmol) and stirred at room temperature for 1 h under argon. The suspension was quenched slowly with water and the organic layer was separated, dried (MgSO₄) and concentrated to afford 9 as a solid (1.96 g, 97%): $^1$H NMR (300 MHz, CDCl₃) δ 2.46 (s, 3, CH₃), 4.84 (s, 2, CH₂OH), 7.15 (m, 2, ArH), 7.29 (m, 1, ArH), 7.65 (m, 1, ArH), 7.92 (br.s, 1, NH).

(b) 5-Carbethoxy-2'-methyl-3,3'-diindolylmethane (12). To a mixture of 2-methylindole-3-carbinol (9) (0.18 g, 1.12 mmol) and ethyl indole-5-carboxylate (10) (0.21 g, 1.1 mmol) in CH₂Cl₂ (5 mL) was added (CF₃SO₃)₃Sc (0.05 g) and stirred for overnight under argon. The solvent was evaporated to give a crude product. Flash chromatography (30% EtOAc/hexane) yielded 12 as a white solid (0.32 g, 87%): $^1$H NMR (300 MHz, CDCl₃) δ 1.43 (t, J=7.1 Hz, 3, CO₂CH₂CH₃), 2.43 (s, 3, CH₃), 4.19 (s, 2, CH₂), 4.41 (q, J=7.1 Hz, 2, CO₂CH₂CH₃), 6.76 (s, 1, PyH), 7.02 (m, 1, ArH), 7.11 (m, 1, ArH), 7.30 (m, 2, ArH), 7.44 (d, J=7.8 Hz, 1, ArH), 7.82 (br.s, 1, NH), 7.91 (dd, J=1.6, 8.7 Hz, 1, ArH), 8.01 (br.s, 1, NH), 8.48 (d, J=1.6 Hz, 1, ArH).

Example 4

Synthesis of 2-Carbethoxy-2'-methyl-3,3'-diindolylmethane (13)

2-Carbethoxy-2'-methyl-3,3'-diindolylmethane (13). To a mixture of 2-methylindole-3-carbinol (9) (0.18 g, 1.12 mmol) and ethyl indole-2-carboxylate (11) (0.21 g, 1.1 mmol) in CH₂Cl₂ (5 mL) was added (CF₃SO₃)₃Sc (0.025 g) and stirred for overnight under argon. The solvent was evaporated to give a crude product. Flash chromatography (20% EtOAc/hexane) yielded 13 as a white solid (0.27 g, 73%): $^1$H NMR (300 MHz, CDCl₃) δ 1.42 (t, J=7.1 Hz, 3, CO₂CH₂CH₃), 2.35 (s, 3, CH₃), 4.48 (q, J=7.1 Hz, 2, CO₂CH₂CH₃), 4.62 (s, 2, CH₂), 6.91 (m, 1, ArH), 6.99 (m, 1, ArH), 7.07 (m, 1, ArH), 7.22 (m, 1, ArH), 7.33 (m, 1, ArH), 7.39 (m, 1, ArH), 7.48 (m, 1, ArH), 7.74 (br.s, 1, NH), 8.77 (br.s, 1, NH).

Scheme III illustrates the reactions of Examples 5-10.

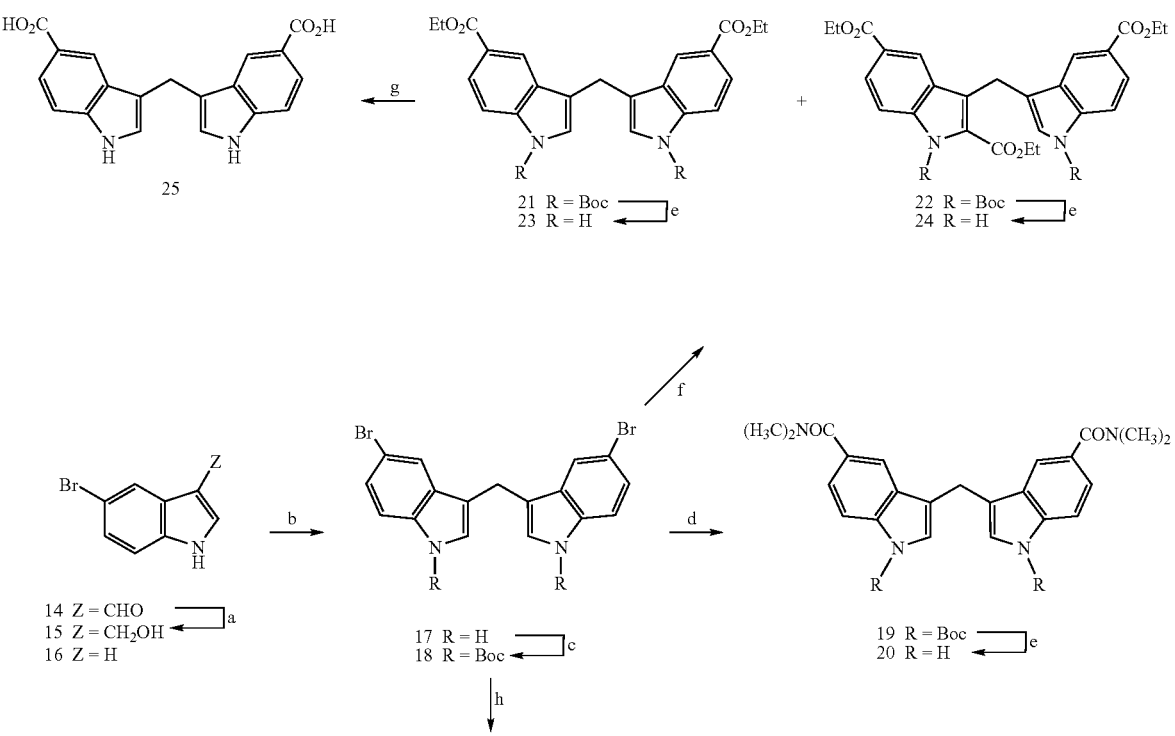

Scheme III.

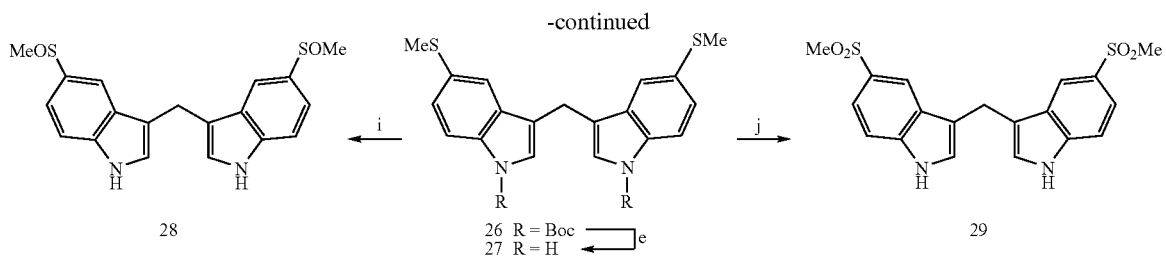

a. NaBH₄.
b. (CF₃SO₃)₃Sc.
c. (t-BuOCO)₂O, DMAP, THF.
d. t-BuLi, ClCON(CH₃)₂.
e. 160° C.
f. t-BuLi, ClCO₂CH₂CH₃.
g. NaOH, CH₃CH₂OH/H₂O.
h. t-BuLi, CH₃SSCH₃.
i. 3-ClC₆H₄CO₃H (2.1 eq.).
j. 3-ClC₆H₄CO₃H (4.2 eq.).

Example 5

Synthesis of 5,5'-Bis(N,N-dimethylcarbamoyl)-3,3'-diindolylmethane (20)

(a) 5-Bromoindole-3-carbinol (15). To a solution of aldehyde 14 (10 g, 44.63 mmol) in THF (100 mL) was added NaBH (2.0 g, 52.9 mmol) slowly at 0° C. under argon and warmed to room temperature for 1 h. The suspension was quenched slowly with water and the organic layer was separated, dried (MgSO₄) and concentrated to afford a solid (9.9 g, 98%): ¹H NMR (300 MHz, CDCl₃) δ 1.47 (t, J=5.5 Hz, 1, CH₂OH), 4.85 (d, J=5.5 Hz, 2, CH₂OH), 7.26 (m, 3, ArH and PyH), 7.88 (d, J=1.8 Hz, 1, ArH), 8.11 (br.s, 1, NH).

(b) 5,5'-Dibromo-3,3'-diindolylmethane (17). To a mixture of 5-bromoindole-3-carbinol (15) (7.76 g, 34.34 mmol) and 5-bromoindole (16) (6.73 g, 34.34 mmol) in CH₂Cl₂ (65 mL) was added (CF₃SO₃)₃Sc (1.0 g, 2.03 mmol) and stirred for overnight under argon. The solvent was evaporated to give a crude product. Flash chromatography (20% EtOAc/hexane) yielded 17 as a white solid (11.2 g, 81%): ¹H NMR (300 MHz, CDCl₃) δ 4.14 (s, 2, CH₂), 6.96 (m, 2, PyH), 7.24 (d, J=8.0 Hz, 2, ArH), 7.28 (dd, J=1.5, 8.0 Hz, 2, ArH), 7.71 (d, J=1.5 Hz, 2, ArH), 7.97 (br.s, 2, NH).

(c) 1,1'-DiBOC-5,5'-dibromo-3,3'-diindolylmethane (18). To a solution of 5,5-dibromo-3,3'-diindolylmethane (17) (7.3 g, 18.06 mmol) and (t-BuOOC)₂O (8.7 g, 39.8 mmol) in THF (100 mL) was added a catalytic amount of dimethylaminopyridine (DMAP) and stirred for overnight under argon. The solvent was evaporated to give a crude product. Flash chromatography (5% EtOAc/hexane) yielded 18 as a white solid (10.3 g, 94%): ¹H NMR (300 MHz, CDCl₃) δ 1.65 (s, 18, OC(CH₃)₃), 4.00 (s, 2, CH₂), 7.34 (s, 2, PyH), 7.42 (dd, J=2.0, 8.2 Hz, 2, ArH), 7.63 (d, J=2.0 Hz, 2, ArH), 8.01 (d, J=8.2 Hz, 2, ArH).

(d) 1,1'-DiBOC-5,5'-bis(N,N-dimethylcarbamoyl)-3,3'-diindolylmethane (19). To a solution of 1.7 M t-BuLi in pentane (4 mL, 6.8 mmol) in THF (20 mL) at −100° C. under argon was added 18 (1.0 g, 1.66 mmol) in THF (5 mL), and stirred for 10 min. Dimethylcarbamyl chloride (2 mL) was added and the mixture was slowly warmed to −5° C. and stirred for overnight. The reaction mixture was poured into saturated aqueous NaHCO₃ and extracted with 80% EtOAc/hexane. The combined organic extracts were dried (MgSO₄), filtered, and concentrated to afford a solid. Flash chromatography (EtOAc/hexane) yielded the desired compound 19 as a white solid (0.79 g, 81%): ¹H NMR (300 MHz, CDCl₃) δ 1.65 (s, 18, OC(CH₃)₃), 3.04 (br.s, 12, N(CH₃)₂), 4.09 (s, 2, CH₂), 7.37 (m, 4, ArH), 7.59 (s, 1, ArH), 8.13 (m, 2, ArH).

(e) 5,5'-Bis(N,N-dimethylcarbamoyl)-3,3'-diindolylmethane (20). 19 (0.79 g, 1.34 mmol) was heated to 160° C. for 5 min. Flash chromatography (EtOAc/hexane) yielded the desired compound 20 as a white solid (0.29 g, 94%): ¹H NMR (300 MHz, CDCl₃) δ 3.05 (br.s, 12, N(CH₃)₂), 3.98 (s, 2, CH₂), 6.41 (s, 2, PyH), 7.16 (dd, J=1.3, 8.3 Hz, 2, ArH), 7.23 (d, J=8.3 Hz, 2, ArH), 7.59 (d, J=1.3 Hz, 2, ArH), 8.96 (br.s, 2, NH).

Example 6

Synthesis of 5,5'-Dicarbethoxy-3,3'-diindolylmethane (23) and 2,5,5'-Tricarbethoxy-3,3'-diindolylmethane (24)

5,5'-Dicarbethoxy-3,3'-diindolylmethane (23) and 2,5,5'-Tricarbethoxy-3,3'-diindolylmethane (24). To a solution of 1.7 M t-BuLi in pentane (4.9 mL, 8.27 mmol) in THF (20 mL) at −100° C. under argon was added 18 (1.0 g, 1.66 mmol) in THF (5 mL), and stirred for 10 min. ClCO₂CH₂CH₃ (1 mL) was added to the solution and stirred for 20 min. The reaction mixture was poured into saturated aqueous NaHCO₃ and extracted with 50% EtOAc/hexane. The combined organic extracts were dried (MgSO₄), filtered, and concentrated to afford a crude products of 1,1'-diBOC-5,5'-dicarbethoxy-3,3'-diindolylmethane 21 and 1,1'-diBOC-2,5,5'-tricarbethoxy-3,3'-diindolylmethane (22) (1.2 g), which was heated to 160° C. for 5 min. Flash chromatography (30% EtOAc/hexane) yielded 23 (0.32 g, 50%) and 24 (0.15 g, 20%) as a white solid: 5,5'-Dicarbethoxy-3,3'-diindolylmethane (23), ¹H NMR (300 MHz, CDCl₃) δ 1.39 (t, J=7.1 Hz, 6, CO₂CH₂CH₃), 4.30 (s, 2, CH₂), 4.38 (q, J=7.1 Hz, 4, CO₂CH₂CH₃), 7.00 (s, 2, PyH), 7.35 (d, J=8.8 Hz, 2, ArH), 7.91 (dd, J=1.6, 8.8 Hz, 2, ArH), 8.19 (br.s, 2, NH), 8.39 (d, J=1.6 Hz, 2, ArH). 2,5,5'-Tricarbethoxy-3,3'-diindolylmethane (24), ¹H NMR (300 MHz, CDCl₃) δ 1.34 (t, J=7.1 Hz, 3, CO₂CH₂CH₃), 1.36 (t, J=7.1 Hz, 6, CO₂CH₂CH₃), 1.42 (t, J=7.1 Hz, 6, CO₂CH₂CH₃), 4.35 (q, J=7.1 Hz, 2, CO₂CH₂CH₃), 4.40 (q, J=7.1 Hz, 2, CO₂CH₂CH₃), 4.43 (q, J=7.1 Hz, 2, CO₂CH₂CH₃), 4.69 (s, 2, CH₂), 6.84 (s, 1, PyH), 7.33 (d, J=8.7 Hz, 1, ArH), 7.41 (d, J=8.7 Hz, 1, ArH), 7.91 (dd, J=1.5, 8.7 Hz, 1, ArH), 8.00 (dd, J=1.5, 8.7 Hz, 1, ArH), 8.07 (br.s, 1, NH), 8.43 (d, J=1.5 Hz, 1, ArH), 8.52 (d, J=1.5 Hz, 1, ArH), 8.95 (br.s, 1, NH).

Example 7

Synthesis of 5,5'-Dicarboxy-3,3'-diindolylmethane (25)

5,5'-Dicarboxy-3,3'-diindolylmethane (25). To a suspension of the ester 23 (0.199 mmol) in 75% aq. EtOH (8 mL) was added one pellet of NaOH (~0.11 g), and the mixture was stirred at 70° C. for 1 h during which time the compound dissolved. The solution was cooled to room temperature, concentrated, added $H_2O$ (5 mL), and then acidified with 1 N HCl. The white precipitate was filtered and dried under vacuum to afford 25 as a solid (0.11 g, 86%): $^1$H NMR (300 MHz, CDCl$_3$) δ 4.27 (s, 2, CH$_2$), 7.08 (s, 2, PyH), 7.36 (d, J=8.6 Hz, 2, ArH), 7.78 (dd, J=1.5, 8.6 Hz, 2, ArH), 8.31 (d, J=1.5 Hz, 2, ArH).

Example 8

Synthesis of 5,5'-dimethylthio-3,3'-diindolylmethane (27)

5,5'-Dimethylthio-3,3'-diindolylmethane (27). To a solution of 1.7 M t-BuLi in pentane (4.9 mL, 8.27 mmol) in THF (20 mL) at −100° C. under argon was added 18 (1.0 g, 1.66 mmol) in THF (5 mL), and stirred for 10 min. Methyldisulfide (1 mL) was added and the mixture was slowly warmed to room temperature. The reaction mixture was poured into saturated aqueous NaHCO$_3$ and extracted with 50% EtOAc/hexane. The combined organic extracts were dried (MgSO$_4$), filtered, and concentrated to afford a solid. Flash chromatography (5% EtOAc/hexane) yielded the desired compound 26 as a solid (0.5 g, 56%). Compound 26 was heated to 160° C. for 5 min, and the residue was subjected to chromatography (20% EtOAc/hexane) to give 27 as a solid (0.13 g, 63%): $^1$H NMR (300 MHz, CDCl$_3$) δ 2.48 (s, 6, SCH$_3$), 4.20 (s, 2, CH$_2$), 6.95 (s, 2, PyH), 7.22 (dd, J=1.7, 8.3 Hz, 2, ArH), 7.30 (d, J=8.3 Hz, 2, ArH), 7.62 (d, J=1.7 Hz, 2, ArH), 7.93 (br.s, 2, NH).

Example 9

Synthesis of 5,5'-Dimethylsulfinyl-3,3'-diindolylmethane (28)

5,5'-Dimethylsulfinyl-3,3'-diindolylmethane (28). To a solution of 27 (0.1 g, 0.29 mmol), in CH$_2$Cl$_2$ (5 mL) at room temperature under argon was added mCPBA (0.14 g, 0.6 mmol), and stirred for 10 min. The reaction mixture was directly subjected to flash chromatography (80% EtOAc/hexane) to yield 28 as a solid (0.08 g, 82%): $^1$H NMR (300 MHz, CDCl$_3$) δ 3.08 (s, 6, SOCH$_3$), 4.28 (s, 2, CH$_2$), 7.10 (s, 2, PyH), 7.49 (d, J=8.5 Hz, 2, ArH), 7.70 (d, J=8.5 Hz, 2, ArH), 8.20 (s, 2, ArH), 8.55 (br.s, 2, NH).

Example 10

Synthesis of 5,5'-Dimethylsulfonyl-3,3'-diindolylmethane (29)

5,5'-Dimethylsulfonyl-3,3'-diindolylmethane (29). To a solution of 27 (0.05 g, 0.15 mmol), in CH$_2$Cl$_2$ (2 mL) at room temperature under argon was added mCPBA (0.14 g, 0.6 mmol), and stirred for 1 h. The reaction mixture was directly subjected to flash chromatography (10% EtOAc/hexane) to yield 29 as a solid (0.04 g, 70%): $^1$H NMR (300 MHz, CDCl$_3$) δ 2.75 (s, 6, SO$_2$CH$_3$), 4.20 (s, 2, CH$_2$), 6.96 (s, 2, PyH), 7.40 (d, J=8.6 Hz, 2, ArH), 7.46 (d, J=8.6 Hz, 2, ArH), 7.93 (s, 2, ArH), 8.76 (br.s, 2, NH).

Scheme IV illustrates the reactions of Examples 11 and 12.

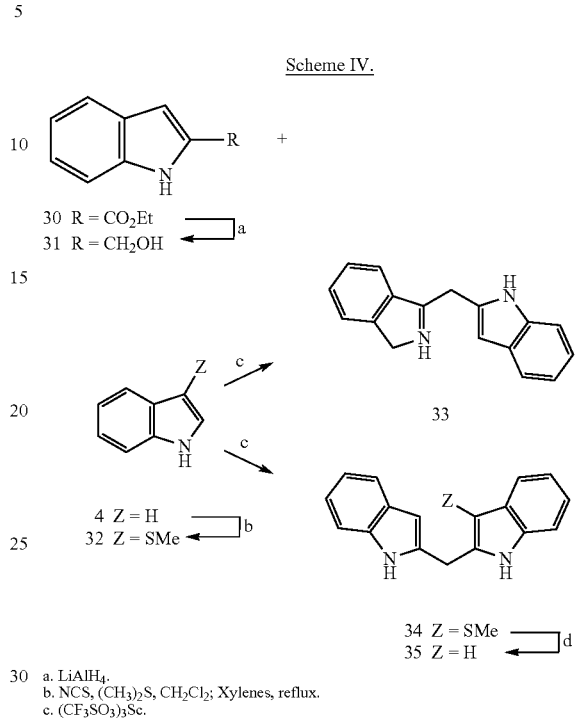

Scheme IV.

30 R = CO$_2$Et
31 R = CH$_2$OH
4 Z = H
32 Z = SMe
34 Z = SMe
35 Z = H a. LiAlH$_4$.
b. NCS, (CH$_3$)$_2$S, CH$_2$Cl$_2$; Xylenes, reflux.
c. (CF$_3$SO$_3$)$_3$Sc.
d. Raney Ni, EtOH.

General procedures used in Examples 14-24: Presented below are the general methods used for the syntheses of indole analogs.

(a) Boc Deprotection. To a solution of Boc-protected indole (6.24 mmol) in CH$_2$Cl$_2$ (50 mL) was added CF$_3$CO$_2$H (10 mL) and stirred for overnight under argon. The solution was diluted with toluene (30 mL) and evaporated to give a solid, which was then subjected to recrystallization.

(b) Halogen-metal exchange and nuclei addition. To a solution of 1.7 M t-BuLi in pentane (22.5 mmol) in THF (70 mL) at −100° C. under argon was added N-protected dibromoindole (5.11 mmol) in THF (10 mL), and stirred for 10 min. Excess amount of ClCO$_2$CH$_2$CH$_3$ (5 mL) was added and the mixture was stirred for 20 min. The reaction mixture was poured into saturated aqueous NaHCO$_3$ and extracted with 50% EtOAc/hexane. The combined organic extracts were dried (MgSO$_4$), filtered, and concentrated. The crude products were subjected to chromatography.

Example 11

Synthesis of 2,3'-Diindolylmethane (33)

(a) Indole-2-carbinol (31). To a solution of ester 30 (7.5 g, 39.64 mmol) in ether (100 mL) was added LiAlH$_4$ (2.3 g, 60.6 mmol) slowly at 0° C. under argon and warmed to room temperature for 1 h. The suspension was quenched with water and white precipitate was removed by filtration. The filtrate was dried (MgSO$_4$) and concentrated to afford 31 as a solid (5.75 g, 98%): $^1$H NMR (300 MHz, CDCl$_3$) δ 4.82 (s, 2, CH$_2$OH), 6.41 (s, 1, PyH), 7.11 (m, 1, ArH), 7.20 (m, 1, ArH), 7.35 (d, J=7.8 Hz, 1, ArH), 7.59 (d, J=7.7 Hz, 1, ArH), 8.35 (br.s, 1, NH).

(b) 2,3'-Diindolylmethane (33). To a mixture of indole-2-carbinol (31) (0.5 g, 3.4 mmol) and indole (4) (0.4 g, 3.4 mmol) in $CH_2Cl_2$ (15 mL) was added $(CF_3SO_3)_3Sc$ (0.17 g, 0.34 mmol) and stirred for 4 h under argon. The solvent was evaporated to give a crude product. Flash chromatography (200 EtOAc/hexane) yielded 33 as a white solid (0.52 g, 63%): $^1$H NMR (300 MHz, $CDCl_3$) δ 4.30 (s, 2, $CH_2$), 6.41 (s, 2, PyH), 7.03-7.14 (m, 4, ArH, PyH), 7.17-7.26 (m, 2, ArH), 7.39 (d, J=8.2 Hz, 1, ArH), 7.55 (m, 1, ArH), 7.57 (m, 1, ArH), 7.85 (br.s, 1, NH), 7.99 (br.s, 1, NH).

Example 12

Synthesis of 2,2'-Diindolylmethane (35)

(a) 3-Methylthioindole (32). To a solution of succinimide-dimethylsulfonium chloride in $CH_2Cl_2$, prepared by the addition of $(CH_3)_2S$ (1.8 mL, 23.5 mmol) to a solution of NCS (3.14 g, 23.5 mmol) in $CH_2Cl_2$ (60 mL) at 0° C., was added indole (4) (2.5 g, 21.33 mmol) in $CH_2Cl_2$ (15 mL) at −20° C. under argon. The reaction mixture was slowly warmed to room temperature for 1 h. After removal of the solvent, 3-dimethylsulfoniumindole and succinimide were obtained quantitatively. The salt was dissolved in xylene and the mixture was heated to reflux for 30 min Flash chromatography (10% EtOAc/hexane) yielded 32 as an oil (3.2 g, 93%): $^1$H NMR (300 MHz, $CDCl_3$) δ 2.39 (s, 3, $SCH_3$), 7.22 (m, 1, PyH), 7.26 (m, 1, ArH), 7.31 (d, J=2.5 Hz, 1, ArH), 7.39 (m, 1, ArH), 7.79 (m, 1, ArH), 8.09 (br.s, 1, NH).

2,2'-Diindolylmethane (35). To a mixture of indole-2-carbinol (31) (0.45 g, 3.06 mmol) and 3-methylthioindole (32) (0.5 g, 3.06 mmol) in $CH_2Cl_2$ (10 mL) was added $(CF_3SO_3)_3Sc$ (0.2 g, 0.49 mmol) and stirred for 3 h under argon. The solvent was evaporated to give a crude product 34. The crude 34 was dissolved in EtOH (10 mL) and Raney Ni was added at room temperature until no starting material was observed from TLC. The Raney Ni was removed by filtration and washed with ethyl acetate. The filtrate was dried ($MgSO_4$) and concentrated to give a solid. Flash chromatography (10% EtOAc/hexane) yielded 35 as a white solid (0.49 g, 65%): $^1$H NMR (300 MHz, $CDCl_3$) δ 4.31 (s, 2, $CH_2$), 6.46 (s, 2, PyH), 7.11 (m, 2, ArH), 7.15 (m, 2, ArH), 7.25 (m, 2, ArH), 7.59 (m, 2, ArH), 7.88 (br.s, 2, NH).

Scheme V illustrates the reactions of Examples 13 and 14.

Scheme V.

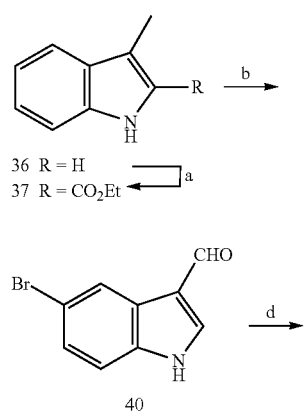

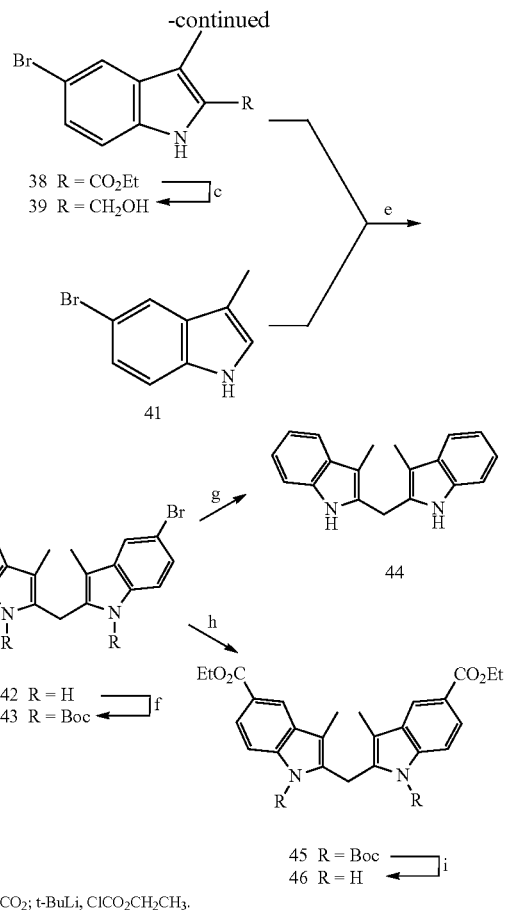

a. n-BuLi, $CO_2$; t-BuLi, $ClCO_2CH_2CH_3$.
b. NBS.
c. $LiAlH_4$.
d. $LiAlH_4$, 60° C.
e. $(CF_3SO_3)_3Sc$.
f. $(t-BuOCO)_2O$, DMAP.
g. Raney Ni.
h. t-BuLi; $ClCO_2CH_2CH_3$.
i. $CF_3CO_2H$.

Example 13

Synthesis of 3,3'-Dimethyl-2,2'-diindolylmethane (44)

(a) Ethyl 3-methylindole-2-carboxylate (37). To a solution of 3-methylindole (36) (4.06 g, 30.9 mmol) in 85 mL of THF was added 2.5 M n-BuLi (34 mmol) in hexane (13.6 mL) at −78° C. under argon, and the white precipitate appeared instantly. This suspension was stirred for 10 min and $CO_2$ gas was passed through the reaction mixture until the solution become clear. The reaction mixture was warmed to room temperature, and the solvent was removed to give a white solid. The white solid was dissolved in 100 mL of THF and then cooled to −78° C. t-BuLi (20.6 mL, 35 mmol) was added and the bright yellow solution was warmed to −35° C. for 10 min; then cooled to −78° C. Ethyl chloroformate (10 mL) was added and stirred for 20 min. The reaction mixture was poured into aqueous $NH_4Cl$ and extracted twice (40% EtOAc/hexane). The extract was dried ($MgSO_4$) and concentrated to afford 37 as a white solid (6.3 g, 100%): $^1$H NMR (300 MHz, $CDCl_3$) δ 1.43 (t, J=7.1 Hz, 3, $CO_2CH_2CH_3$), 2.62

(s, 3, CH$_3$), 4.42 (q, J=7.1 Hz, 2, CO$_2$CH$_2$CH$_3$), 7.14 (m, 1, ArH), 7.33 (m, 2, ArH), 7.67 (dd, J=0.9, 8.1 Hz, 1, ArH), 8.66 (br.s, 1, NH).

(b) Ethyl 5-bromo-3-methylindole-2-carboxylate (38). To a solution of ester 37 (2.6 g, 12.8 mmol) and CF$_3$CO$_2$H (2 mL) in THF (40 mL) was added NBS (2.3 g, 12.9 mmol) at room temperature. The reddish solution was stirred for 5 min, quenched with aqueous Na$_2$S$_2$O$_3$, and extracted twice (40% EtOAc/hexane). The extract was washed with aqueous NaHCO$_3$; dried (MgSO$_4$) and concentrated to afford a solid. Flash chromatography (10% EtOAc/hexane) yielded 38 as a white solid (3.43 g, 95%): $^1$H NMR (300 MHz, CDCl$_3$) δ 1.43 (t, J=7.1 Hz, 3, CO$_2$CH$_2$CH$_3$), 2.56 (s, 3, CH$_3$), 4.42 (q, J=7.1 Hz, 2, CO$_2$CH$_2$CH$_3$), 7.25 (d, J=8.9 Hz, 1, ArH), 7.39 (dd, J=1.8, 8.9 Hz, 1, ArH), 7.80 (d, J=1.8 Hz, 1, ArH), 8.71 (br.s, 1, NH).

(c) 5-Bromo-3-methylindole-2-carbinol (39). To a solution of ester 38 (3.4 g, 12.05 mmol) in THF (60 mL) was added LiAlH$_4$ (0.95 g, 25 mmol) at 0° C. under argon and stirred for 2 h. The suspension was quenched slowly with water and white precipitate was removed by filtration. The filtrate was dried (MgSO$_4$) and concentrated to afford 39 as a solid (2.8 g, 97%): $^1$H NMR (300 MHz, CDCl$_3$) δ 2.24 (s, 3, CH$_3$), 4.83 (s, 2, CH$_2$OH), 7.19 (m, 1, ArH), 7.25 (m, 1, ArH), 7.65 (m, 1, ArH), 8.21 (br.s, 1, NH).

(d) 5,5'-Dibromo-3,3'-dimethyl-2,2'-diindolylmethane (42). To a solution of aldehyde 40 (1.51 g, 6.74 mmol) in THF (35 mL) was added LiAlH$_4$ (0.51 g, 13.48 mmol) at 0° C. and then heated to 65-70° C. for 2 h under argon. The suspension was cooled to 0° C. and quenched with water, and white precipitate was removed by filtration. The filtrate was dried (MgSO$_4$) and concentrated to afford 5-bromo-3-methylindole (41) as a solid (1.16 g, 82%). To a mixture of 39 (1.2 g, 5.0 mmol) and 41 (1.0 g, 4.76 mmol) in CH$_2$Cl$_2$ (25 mL) was added (CF$_3$SO$_3$)$_3$Sc (0.23 g, 0.47 mmol) and stirred overnight under argon. The solvent was evaporated to give a crude product. Flash chromatography (10% EtOAc/hexane) yielded 42 as a white solid (1.91 g, 93%): $^1$H NMR (300 MHz, CDCl$_3$) δ 2.29 (s, 6, CH$_3$), 4.21 (s, 2, CH$_2$), 7.08 (d, J=8.5 Hz, 2, ArH), 7.22 (dd, J=1.8, 8.5 Hz, 2, ArH), 7.66 (d, J=1.8 Hz, 2, ArH), 7.67 (br.s, 2, NH).

(e) 3,3'-Dimethyl-2,2'-diindolylmethane (44). 42 (0.29 g, 0.67 mmol) was dissolved in EtOH (4 mL) and Raney Ni was added at room temperature until no starting material was observed from TLC. The Raney Ni was removed by filtration and washed with ethyl acetate. The filtrate was dried (MgSO$_4$) and concentrated to give a solid. Flash chromatography (10% EtOAc/hexane) yielded 44 as a white solid (0.17 g, 91%): $^1$H NMR (300 MHz, CDCl$_3$) δ 2.36 (s, 6, CH$_3$), 4.24 (s, 2, CH$_2$), 7.14 (m, 4, ArH), 7.20 (m, 2, ArH), 7.56 (m, 2, ArH), 7.61 (br.s, 2, NH).

Example 14

Synthesis of 5,5'-Dicarbethoxy-3,3'-dimethyl-2,2'-diindolylmethane (46)

(a) 1,1'-DiBOC-5,5'-dibromo-3,3'-dimethyl-2,2'-diindolylmethane (43). To a solution of indole 42 (1.5 g, 3.47 mmol) and (t-BuOOC)$_2$O (1.82 g, 8.3 mmol) in THF (15 mL) was added a catalytic amount of DMAP and stirred for overnight under argon. The solvent was evaporated to give a crude product. Flash chromatography (5% EtOAc/hexane) yielded the 43 as a white solid (1.75 g, 80%): $^1$H NMR (300 MHz, CDCl$_3$) δ 1.52 (s, 18, OC(CH$_3$)$_3$), 1.84 (s, 6, CH$_3$), 4.78 (s, 2, CH$_2$), 7.35 (dd, J=2.0, 8.8 Hz, 2, ArH), 7.53 (d, J=2.0 Hz, 2, ArH), 7.96 (d, J=8.8 Hz, 2, ArH).

(b) 1,1'-DiBOC-5,5'-dicarbethoxy-3,3'-dimethyl-2,2'-diindolylmethane (45). The general procedure (b) was used to prepare 45 from 43 (1.0 g, 1.58 mmol), 1.7 M t-BuLi in pentane (4.0 mL, 6.8 mmol), and ClCO$_2$CH$_2$CH$_3$ (3 mL). Flash chromatography (10% EtOAc/hexane) yielded 45 as a white solid (0.6 g, 61%): $^1$H NMR (300 MHz, CDCl$_3$) δ 1.42 (t, J=7.1 Hz, 6, CO$_2$CH$_2$CH$_3$), 1.53 (s, 18, OC(CH$_3$)$_3$), 1.94 (s, 6, CH$_3$), 4.40 (q, J=7.1 Hz, 4, CO$_2$CH$_2$CH$_3$), 4.82 (s, 2, CH$_2$), 7.97 (dd, J=1.7, 8.8 Hz, 2, ArH), 8.10 (d, J=8.8 Hz, 2, ArH), 8.15 (d, J=1.7 Hz, 2, ArH).

(c) 5,5'-Dicarbethoxy-3,3'-dimethyl-2,2'-diindolylmethane (46). 45 (0.6 g, 0.97 mmol) was deprotected using the general procedure. Recrystallization (ethyl acetate/hexane) afforded 46 as a white solid (0.38 g, 93%): $^1$H NMR (300 MHz, CDCl$_3$) δ 1.43 (t, J=7.1 Hz, 6, CO$_2$CH$_2$CH$_3$), 2.38 (s, 6, CH$_3$), 4.26 (s, 2, CH$_2$), 4.41 (q, J=7.1 Hz, 4, CO$_2$CH$_2$CH$_3$), 7.21 (d, J=8.5 Hz, 2, ArH), 7.86 (dd, J=1.6, 8.5 Hz, 2, ArH), 7.87 (br.s, 2, NH), 8.31 (d, J=1.6 Hz, 2, ArH).

Example 15

Synthesis of 5,5'-Dicarbethoxy-2,3'-dimethyl-2',3-diindolylmethane (53)

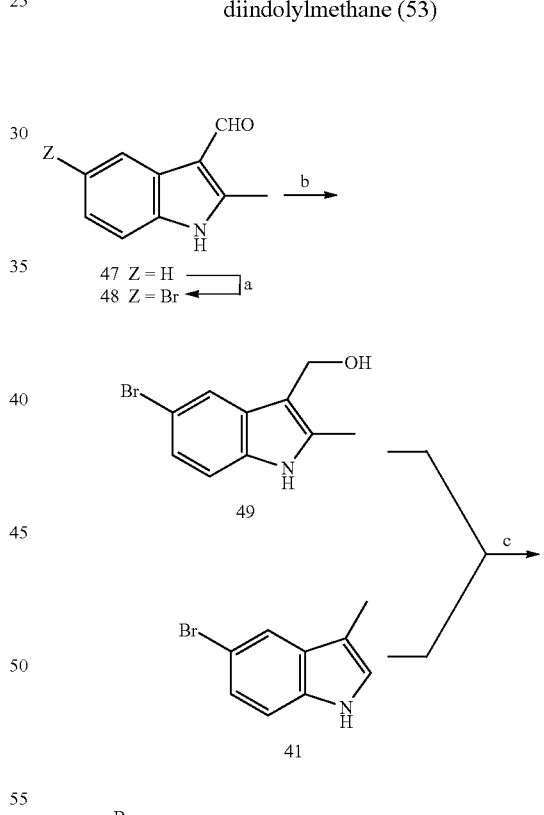

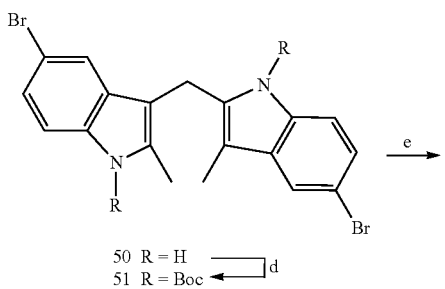

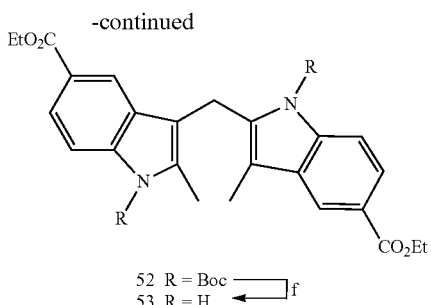

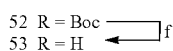

a. NBS.
b. NaBH$_4$.
c. Sc(OTf)$_3$.
d. (t-BuOCO)$_2$O, DMAP.
e. t-BuLi; ClCO$_2$CH$_2$CH$_3$.
f. CF$_3$CO$_2$H.

(a) 5-Bromo-2-methyl-indole-3-carboxaldehyde (48). To a solution of aldehyde 47 (4.18 g, 26.26 mmol) in CH$_2$Cl$_2$ (40 mL) was added NBS (4.67 g, 26.26 mmol) and stirred for 15 min under argon. The reddish solution was poured into aqueous Na$_2$S$_2$O$_3$, and extracted twice (50% EtOAc/hexane). The extract was washed with aqueous NaHCO$_3$; dried (MgSO$_4$) and concentrated to afford a solid. Flash chromatography (40% EtOAc/hexane) yielded 48 as a solid (5.83 g, 93%): $^1$H NMR (300 MHz, CDCl$_3$) δ 2.73 (s, 3, CH$_3$), 7.36 (dd, J=1.5, 8.5 Hz, 1, ArH), 7.47 (d, J=1.5 Hz, 1, ArH), 8.10 (d, J=8.5 Hz, 1, ArH), 8.40 (br.s, 1, NH), 10.16 (s, 1, CHO).

(b) 1,1′-DiBOC-5,5′-dibromo-2,3′-dimethyl-2′,3-diindolylmethane (51). To a solution of aldehyde 48 (1.0 g, 4.2 mmol) in wet THF (20 mL) was added NaBH$_4$ (0.18 go 4.6 mmol) at room temperature and stirred for 1 h under argon. The suspension was quenched slowly with water and the organic layer was separated, dried (MgSO$_4$) and concentrated to afford 49 as a solid (1.0 g) in quantitative yield. To a mixture of 5-bromo-2-methylindole-3-carbinol (49) (0.24 g, 1.0 mmol) and 5-bromo-3-methylindole (41) (0.21 g, 1.0 mmol) in CH$_2$Cl$_2$ (5 mL) was added (CF$_3$SO$_3$)$_3$Sc (0.05 g, 0.1 mmol) and stirred for overnight under argon. The solvent was evaporated to give a crude product. Flash chromatography (20% EtOAc/hexane) yielded 5,5′-dibromo-2,3′-dimethyl-2′,3-diindolylmethane (50) as a white solid (0.38 g, 88%). To a solution of 50 (0.38 g, 0.88 mmol) and (t-BuOOC)$_2$O (0.42 g, 1.93 mmol) in THF (15 mL) was added a catalytic amount of DMAP and stirred for overnight under argon. The solvent was evaporated to give a crude product. Flash chromatography (3% EtOAc/hexane) yielded 51 as a white solid (0.51 g, 92%): $^1$H NMR (300 MHz, CDCl$_3$) δ 1.48 (s, 9, OC(CH$_3$)$_3$), 1.67 (s, 9, OC(CH$_3$)$_3$), 2.12 (s, 3, CH$_3$), 2.44 (s, 3, CH$_3$), 4.40 (s, 2, CH$_2$), 6.81 (d, J=8.4 Hz, 1, ArH), 7.13 (dd, J=1.7, 8.4 Hz, 1, ArH), 7.34 (dd, J=1.9, 8.8 Hz, 1, ArH), 7.58 (d, J=1.7 Hz, 1, ArH), 7.84 (d, J=8.8 Hz, 1, ArH), 8.29 (d, J=1.9 Hz, 1, ArH).

(c) 5,5′-Dicarbethoxy-2,3′-dimethyl-2′,3-diindolylmethane (53). The general procedure (b) was used to prepare 52 from 51 (0.5 g, 0.79 mmol), 1.7 M t-BuLi in pentane (2.3 mL, 3.95 mmol), and ClCO$_2$CH$_2$CH$_3$ (3 mL). Flash chromatography (10% EtOAc/hexane) yielded 1,1′-diBOC-5,5′-dicarbethoxy-2,3′-dimethyl-2′,3-diindolylmethane (52) as a white solid (0.43 g, 88%). 52 (0.43 g, 0.69 mmol) was deprotected using the general procedure. Recrystallization (ethyl acetate/hexane) afforded 53 as a white solid (0.25 g, 87%): $^1$H NMR (300 MHz, CDCl$_3$) δ 1.39 (t, J=7.1 Hz, 3, CO$_2$CH$_2$CH$_3$), 1.40 (t, J=7.1 Hz, 3, CO$_2$CH$_2$CH$_3$), 2.40 (s, 3, CH$_3$), 2.42 (s, 3, CH$_3$), 4.18 (s, 2, CH$_2$), 4.37 (q, J=7.1 Hz, 4, CO$_2$CH$_2$CH$_3$), 7.08 (d, J=8.2 Hz, 1, ArH), 7.35 (d, J=8.5 Hz, 1, ArH), 7.67 (br.s, 1, NH), 7.75 (d, J=8.2 Hz, 1, ArH), 7.77 (d, J=8.5 Hz, 1, ArH), 8.05 (s, 1, ArH), 8.14 (br.s, 1, NH), 8.27 (s, 1, ArH).

Scheme VII illustrates the reactions of Examples 16 and 17.

Scheme VII.

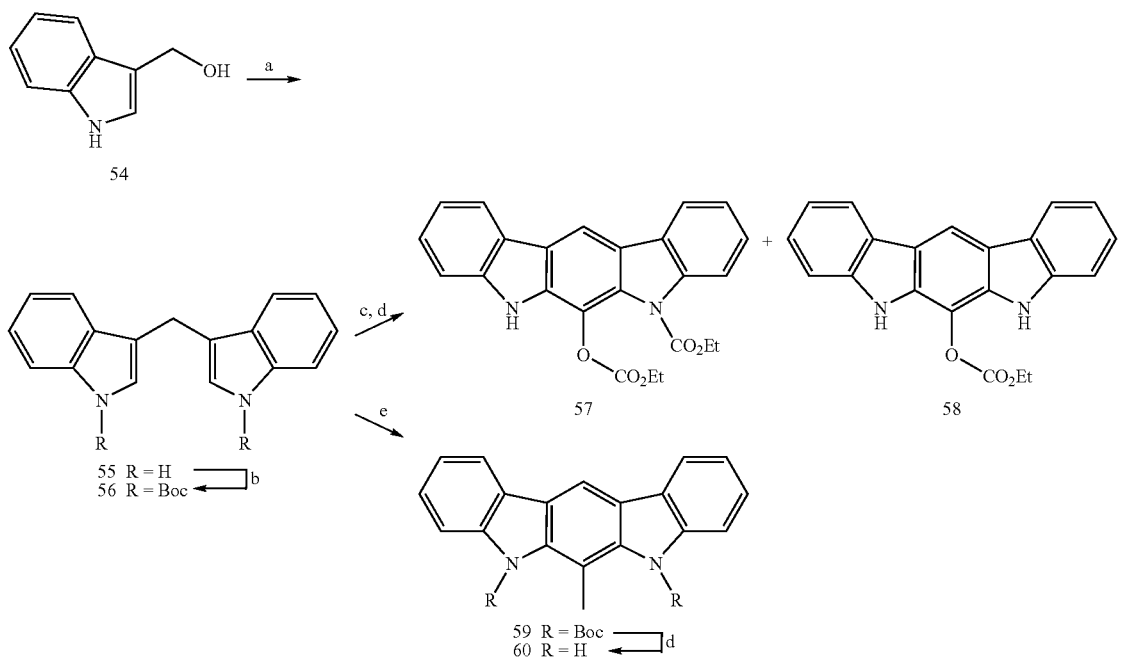

a. aq. NaOH.
b. (t-BuOCO)$_2$O, DMAP.
c. LiTMP; ClCO$_2$CH$_2$CH$_3$.
d. CF$_3$CO$_2$H.
e. LTMP; (CH$_3$CO)$_2$O.

Example 16

Synthesis of 5-Carbethoxy-6-ethoxycarbonyloxy-7H-indolo[2,3-b]carbazole (57) and 6-Ethoxycarbonyloxy-5,7-dihydro-indolo[2,3-b]carbazole (58)

(a) 3,3'-Diindolylmethane (55). Indole-3-carbinol (54) (1.0 g, 6.79 mmol) in 10% aqueous NaOH solution (100 mL) was refluxed for 1 h. The solution was cooled, neutralized with carbon dioxide and the white precipitate was collected by filtration, which was then crystallized from toluene to yield 55 as a white solid (0.65 g, 77%). $^1$H NMR (300 MHz, CDCl$_3$) δ 4.26 (s, 2, CH$_2$), 6.94 (m, 2, PyH), 7.11 (m, 2, ArH), 7.21 (m, 2, ArH), 7.36 (m, 2, ArH), 7.64 (m, 2, ArH), 7.86 (br.s, 2, NH).

(b) 1,1'-DiBOC-3,3'-diindolylmethane (56). To a solution of 55 (2.0 g, 8.12 mmol) and (t-BuOOC)$_2$O (3.9 g, 17.87 mmol) in THF (20 mL) was added a catalytic amount of DMAP and stirred for overnight under argon. The solvent was evaporated to give a crude product. Flash chromatography (3% EtOAc/hexane) yielded 56 as a white solid (3.44 g, 95%): $^1$H NMR (300 MHz, CDCl$_3$) δ 1.65 (s, 18, OC(CH$_3$)$_3$), 4.09 (s, 2, CH$_2$), 7.21 (m, 2, ArH), 7.31 (m, 2, ArH), 7.38 (s, 2, PyH), 7.53 (m, 2, ArH), 8.12 (br.d, J=8.6 Hz, 2, ArH).

(c) 5-Carbethoxy-6-ethoxycarbonyloxy-7H-indolo[2,3-b]carbazole (57) and 6-Ethoxycarbonyloxy-5,7-dihydro-indolo[2,3-b]carbazole (58). To a solution of 2,2,6,6-tetramethylpiperidine (1.7 mL, 10 mmol) in THF (25 mL) at −78° C. under argon was added 1.6 M n-BuLi (9.4 mmol) in hexane (6.6 mL), and warmed to 0° C. for 15 min. After the reaction mixture was recooled to −78° C., 56 (0.7 g, 1.57 mmol) in THF (5 mL) was added slowly, and stirring was continued for 30 min before ClCO$_2$CH$_2$CH$_3$ (2 mL) was added. The reaction mixture was stirred for 2 h at −78° C. and poured into saturated NaHCO$_3$ and extracted with 50% EtOAc/hexane. The combined organic extracts were dried (MgSO$_4$), filtered, and concentrated to afford a crude mixture, which was then deprotected using the general procedure. Flash chromatography (20% EtOAc/hexane) yielded 57 (0.1 g, 15%) and 58 (0.39 g, 72%) as a white solid. 5-Carbethoxy-6-ethoxycarbonyloxy-7H-indolo[2,3-b]carbazole (57): $^1$H NMR (300 MHz, CDCl$_3$) δ 1.40 (t, J=7.1 Hz, 3, CO$_2$CH$_2$CH$_3$), 1.46 (t, J=7.1 Hz, 3, CO$_2$CH$_2$CH$_3$), 4.36 (q, J=7.1 Hz, 2, CO$_2$CH$_2$CH$_3$), 4.48 (q, J=7.1 Hz, 2, CO$_2$CH$_2$CH$_3$), 7.22 (m, 1, ArH), 7.30-7.42 (m, 4, ArH), 8.01 (m, 1, ArH), 8.08 (m, 2, ArH), 8.26 (br.s, 1, NH), 8.43 (s, 1, ArH). 6-Ethoxycarbonyloxy-5,7-dihydro-indolo[2,3-b]carbazole (58): $^1$H NMR (300 MHz, CDCl$_3$) δ 1.51 (t, J=7.1 Hz, 3, CO$_2$CH$_2$CH$_3$), 4.49 (q, J=7.1 Hz, 2, CO$_2$CH$_2$CH$_3$), 7.28 (m, 2, ArH), 7.41 (m, 2, ArH), 7.46 (br.d, J=7.8 Hz, 2, ArH), 8.16 (d, J=7.7 Hz, 2, ArH), 8.21 (br.s, 2, NH), 8.60 (s, 1, ArH).

Example 17

Synthesis of 6-Methyl-indolo[2,3-b]carbazole (60)

(a) 6-Methyl-5,7-diBOC-indolo[2,3-b]carbazole (59). To a solution of 2,2,6,6-tetramethylpiperidine (3.5 g, 24.8 mmol) in THF (40 mL) at −78° C. under argon was added 1.6 M n-BuLi (22.4 mmol) in hexane (14 mL), and warmed to 0° C. for 15 min. After the reaction mixture was recooled to −78° C., 56 (1 g, 2.24 mmol) in THF (5 mL) was added slowly, and stirring was continued for 30 min before acetic anhydride (8 mL) was added. The mixture was slowly warmed to 0° C. for 30 min. The reaction mixture was poured into saturated NaHCO$_3$ and extracted with 50% EtOAc/hexane. The combined organic extracts were dried (MgSO$_4$), filtered, and concentrated to afford a crude product. Flash chromatography (5% EtOAc/hexane) yielded 59 as a white solid (0.98 g, 93%): $^1$H NMR (300 MHz, CDCl$_3$) δ 1.75 (s, 18, OC(CH$_3$)$_3$), 2.54 (s, 3, CH$_3$), 7.37 (m, 2, ArH), 7.45 (m, 2, ArH), 8.05 (dd, J=1.7, 8.0 Hz, 2, ArH), 8.11 (dd, J=1.7, 8.0 Hz, 2, ArH), 8.35 (s, 1, ArH).

(b) 6-Methyl-5,7-dihydro-indolo[2,3-b]carbazole (60). 59 (0.98 g, 2.08 mmol) was deprotected using the general procedure. Recrystallization (ethyl acetate/hexane) afforded 60 as a white solid (0.51 g, 91%): $^1$H NMR (300 MHz, CDCl$_3$) δ 2.69 (s, 3, CH$_3$), 7.26 (m, 2, ArH), 7.38 (d, J=7.7 Hz, 2, ArH), 7.44 (m, 2, ArH), 7.90 (br.s, 2, ArH), 8.16 (d, J=7.7 Hz, 2, ArH), 8.59 (s, 1, ArH).

Scheme VIII illustrates the reactions of Examples 18-22:

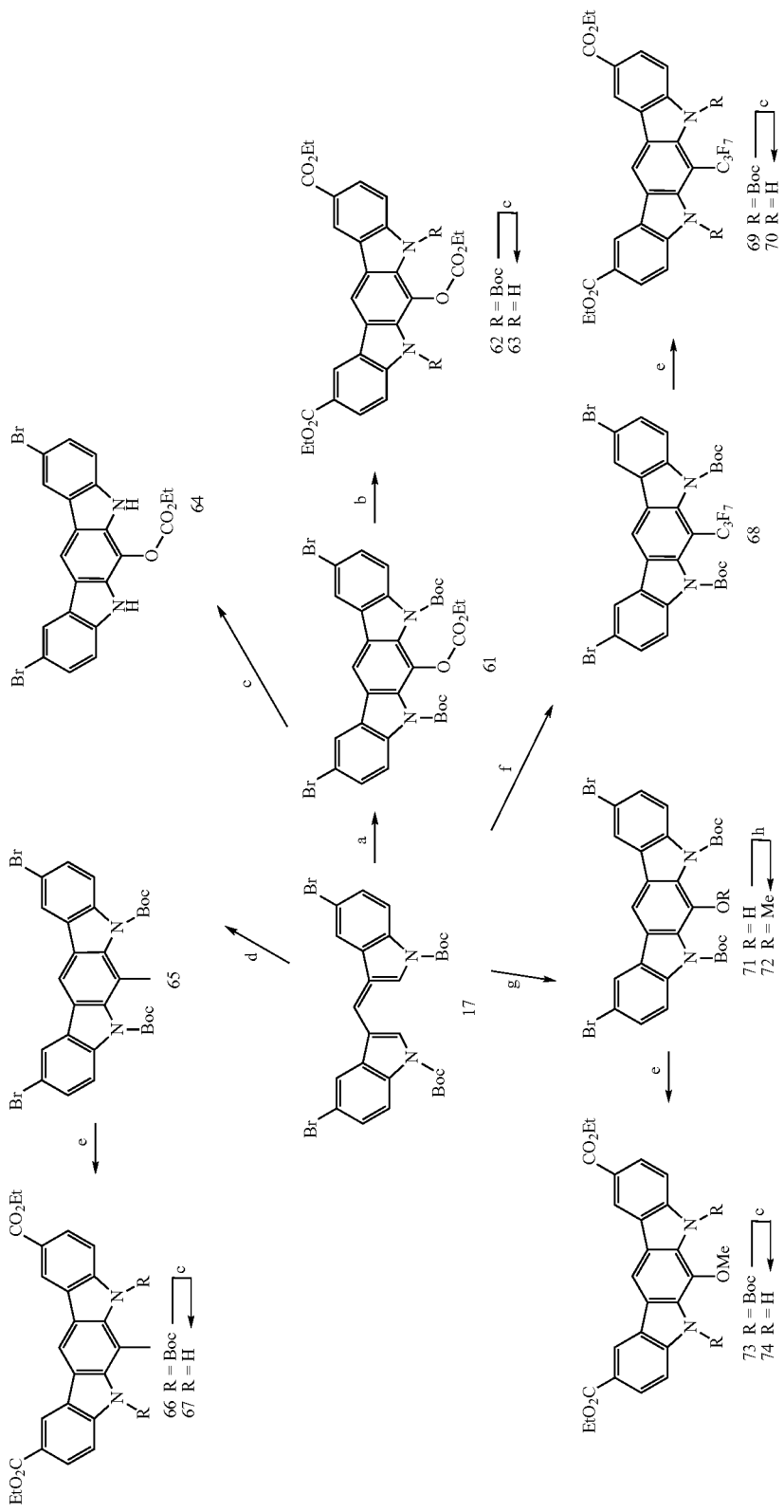
Scheme VIII
a. LiTMP; ClCO₂CH₂CH₃.
b. t-BuLi (5.5 eq.); ClCO₂CH₂CH₃.
c. CF₃CO₂H.
d. LiTMP; (CH₃CO)₂O.
e. t-BuLi (4.4 eq.); ClCO₂CH₂CH₃.
f. LiTMP; (C₃F₇CO)₂O.
g. LiTMP; ClCO₂CH₂CH₃; CH₃CO₂H.
h. CH₃I, K₂CO₃, DMF.

Example 18

Synthesis of 2,10-Dicarbethoxy-6-ethoxycarbonyloxy-5,7-dihydro-indolo[2,3-b]carbazole (63)

(a) 2,10-Dibromo-6-ethoxycarbonyloxy-5,7-diBOC-indolo[2,3-b]carbazole (61). To a solution of 2,2,6,6-tetramethylpiperidine (20.3 g, 143.5 mmol) in THF (300 mL) at −78° C. under argon was added 1.6 M n-BuLi (130.4 mmol) in hexane (81.5 mL), and warmed to 0° C. for 15 min. After the reaction mixture was recooled to −78° C., 17 (7.88 g, 13.04 mmol) in THF (15 mL) was added slowly, and stirring was continued for 30 min before $ClCO_2CH_2CH_3$ (30 mL) was added. The mixture was slowly warmed to −10° C. during 2 h. The reaction mixture was poured into saturated $NaHCO_3$ and extracted with 50% EtOAc/hexane. The combined organic extracts were dried ($MgSO_4$), filtered, and concentrated to afford a crude product. Flash chromatography (5% EtOAc/hexane) yielded 61 as a white solid (8.6 g, 94%): $^1$H NMR (300 MHz, $CDCl_3$) δ 1.39 (t, J=7.1 Hz, 3, $CO_2CH_2CH_3$), 1.74 (s, 18, $OC(CH_3)_3$), 4.33 (q, J=7.1 Hz, 2, $CO_2CH_2CH_3$), 7.54 (dd, J=2.0, 9.1 Hz, 2, ArH), 7.92 (d, J=9.1 Hz, 2, ArH), 8.15 (d, J=2.0 Hz, 2, ArH), 8.31 (s, 1, ArH).

(b) 2,10-Dicarbethoxy-6-ethoxycarbonyloxy-5,7-dihydro-indolo[2,3-b]carbazole (63). To a solution of 1.7 M t-BuLi in pentane (32.3 mL, 54.8 mmol) in THF (200 mL) at −100° C. under argon was added 61 (7.0 g, 9.97 mmol) in THF (20 mL), and stirred for 10 min. $ClCO_2CH_2CH_3$ (30 mL) was added and the mixture was slowly warmed to −10° C. during 2.5 h. The reaction mixture was poured into saturated aqueous $NH_4Cl$ and extracted with 50% EtOAc/hexane. The combined organic extracts were dried ($MgSO_4$), filtered, and concentrated to afford a crude product. Flash chromatography (10%; 20% EtOAc/hexane) yielded 1,1'-diBOC-2,10-dicarbethoxy-6-ethoxycarbonyloxy-indolo[2,3-b]carbazole 62 as a white solid (6.1 g, 89%). 62 (4.3 g, 6.24 mmol) was deprotected using the general procedure. Recrystallization (ethyl acetate/hexane) afforded 63 as a white solid (2.8 g, 92%): $^1$H NMR (300 MHz, $CDCl_3$) δ 1.50 (m, 9, $CO_2CH_2CH_3$), 4.48 (m, 6, $CO_2CH_2CH_3$), 7.46 (d, J=8.3 Hz, 2, ArH), 8.16 (dd, J=1.5, 8.3 Hz, 2, ArH), 8.49 (br.s, 2, NH), 8.71 (s, 1, ArH), 8.89 (d, J=1.5 Hz, 2, ArH).

Example 19

Synthesis of 2,10-Dibromo-6-ethoxycarbonyloxy-5,7-dihydro-Indolo[2,3-b]carbazole (64)

2,10-Dibromo-6-ethoxycarbonyloxy-5,7-dihydro-indolo[2,3-b]carbazole (64). 61 (0.54 g, 0.77 mmol) was deprotected using the general procedure. Recrystallization (ethyl acetate/hexane) afforded 64 as a white solid (0.34 g, 88%): $^1$H NMR (300 MHz, $CDCl_3$) δ 1.42 (t, J=7.1 Hz, 3, $CO_2CH_2CH_3$), 4.41 (q, J=7.1 Hz, 2, $CO_2CH_2CH_3$), 7.25 (d, J=8.5 Hz, 2, ArH), 7.40 (dd, J=1.8, 8.5 Hz, 2, ArH), 8.16 (d, J=1.8 Hz, 2, ArH), 8.38 (s, 1, ArH), 9.31 (br.s, 1, NH).

Example 20

Synthesis of 2,10-Dicarbethoxy-6-methyl-5,7-dihydro-indolo[2,3-b]carbazole (67)

(a) 2,10-Dibromo-6-methyl-5,7-diBOC-indolo[2,3-b]carbazole (65). To a solution of 2,2,6,6-tetramethylpiperidine (2.9 g, 20.5 mmol) in THF (40 mL) at −78° C. under argon was added 1.6 M n-BuLi (18.4 mmol) in hexane (11.5 mL), and warmed to 0° C. for 15 min. After the reaction mixture was recooled to −78° C., 17 (1.1 g, 1.82 mmol) in THF (10 mL) was added slowly, and stirring was continued for 30 min before acetic anhydride (8 mL) was added. After 10 min, the mixture was warmed to 0° C. for 30 min. The reaction mixture was poured into saturated $NaHCO_3$ and extracted with 50% EtOAc/hexane. The combined organic extracts were dried ($MgSO_4$), filtered, and concentrated to afford a crude product. Flash chromatography (3% EtOAc/hexane) yielded 65 as a white solid (1.04 g, 91%): $^1$H NMR (300 MHz, $CDCl_3$) δ 1.74 (s, 18, $OC(CH_3)_3$), 2.51 (s, 3, $CH_3$), 7.53 (dd, J=1.7, 8.8 Hz, 2, ArH), 7.97 (d, J=8.8 Hz, 2, ArH), 8.15 (d, J=1.7 Hz, 2, ArH), 8.26 (s, 1, ArH).

(b) 2,10-Dicarbethoxy-6-methyl-5,7-diBOC-indolo[2,3-b]carbazole (66). The general procedure (b) was used to prepare 66 from 65 (0.387 g, 0.62 mmol), 1.7 M t-BuLi in pentane (1.8 mL, 3.10 mmol), and $ClCO_2CH_2CH_3$ (1 mL). Flash chromatography (5% EtOAc/hexane) yielded 66 as a white solid (0.17 g, 45%): $^1$H NMR (300 MHz, $CDCl_3$) δ 1.48 (t, J=7.0 Hz, 6, $CO_2CH_2CH_3$), 1.76 (s, 18, $OC(CH_3)_3$), 2.53 (s, 3, $CH_3$), 4.48 (q, J=7.0 Hz, 4, $CO_2CH_2CH_3$), 8.12 (d, J=8.5 Hz, 2, ArH), 8.18 (dd, J=1.7, 8.5 Hz, 2, ArH), 8.53 (s, 1, ArH), 8.78 (d, J=1.7 Hz, 2, ArH).

(c) 2,10-Dicarbethoxy-6-methyl-5,7-dihydro-indolo[2,3-b]carbazole (67). 66 (0.14 g, 0.23 mmol) was deprotected using the general procedure. Recrystallization (ethyl acetate/hexane) afforded 67 as a white solid (0.092 g, 97%): $^1$H NMR (300 MHz, DMSO-$d_6$) δ 1.39 (t, J=7.0 Hz, 6, $CO_2CH_2CH_3$), 2.75 (s, 3, $CH_3$), 4.36 (q, J=7.0 Hz, 4, $CO_2CH_2CH_3$), 7.54 (d, J=8.4 Hz, 2, ArH), 7.99 (d, J=8.4 Hz, 2, ArH), 8.85 (s, 2, ArH), 9.01 (s, 1, ArH), 11.56 (s, 2, NH).

Example 21

Synthesis of 2,10-Dicarbethoxy-6-heptafluoropropyl-5,7-dihydro-indolo[2,3-b]carbazole (70)

(a) 2,10-Dibromo-6-heptafluoropropyl-5,7-diBOC-indolo[2,3-b]carbazole (68). To a solution of 2,2,6,6-tetramethylpiperidine (8.9 g, 63 mmol) in THF (180 mL) at −78° C. under argon was added 1.6 M n-BuLi (60 mmol) in hexane (37.5 mL), and warmed to 0° C. for 15 min. After the reaction mixture was recooled to −78° C., 17 (4 g, 6.62 mmol) in THF (20 mL) was added slowly, and stirring was continued for 30 min before heptafluorobutyric anhydride (25 g) was added. After 10 min, the mixture was warmed to 0° C. for 30 min. The reaction mixture was poured into saturated $NaHCO_3$ and extracted with ethyl acetate. The combined organic extracts were dried ($MgSO_4$), filtered, and concentrated to afford a crude product. Flash chromatography (5% EtOAc/hexane) yielded 68 contaminated with excess reagent. Recrystallization (ethyl acetate/hexane) afforded 68 as a white solid (4.1 g, 79%): $^1$H NMR (300 MHz, $CDCl_3$) δ 1.68 (s, 18, $OC(CH_3)_3$), 7.60 (dd, J=2.0, 8.8 Hz, 2, ArH), 7.98 (d, J=8.8 Hz, 2, ArH), 8.18 (d, J=2.0 Hz, 2, ArH), 8.55 (s, 1, ArH).

(b) 2,10-Dicarbethoxy-6-heptafluoropropyl-5,7-diBOC-indolo[2,3-b]carbazole (69). The general procedure (b) was used to prepare 69 from 68 (4.0 g, 5.11 mmol), 1.7 M t-BuLi in pentane (15 mL, 25.56 mmol), and $ClCO_2CH_2CH_3$ (5 mL). Flash chromatography (10% EtOAc/hexane) yielded 69 as a white solid (3.58 g, 91%): $^1$H NMR (300 MHz, $CDCl_3$) δ 1.49 (t, J=7.0 Hz, 6, $CO_2CH_2CH_3$), 1.70 (s, 18, $OC(CH_3)_3$), 4.48 (q, J=7.0 Hz, 4, $CO_2CH_2CH_3$), 8.13 (d, J=8.8 Hz, 2, ArH), 8.23 (dd, J=1.7, 8.8 Hz, 2, ArH), 8.80 (m, 3, ArH).

(c) 2,10-Dicarbethoxy-6-heptafluoropropyl-5,7-dihydro-indolo[2,3-b]carbazole (70). 69 (3.58 g, 4.66 mmol) was deprotected using the general procedure. Recrystallization (ethyl acetate/hexane) afforded 70 as a white solid (2.6 g, 98%): $^1$H NMR (300 MHz, CDCl$_3$) δ 1.50 (t, J=7.3 Hz, 6, CO$_2$CH$_2$CH$_3$), 4.47 (q, J=7.3 Hz, 4, CO$_2$CH$_2$CH$_3$), 7.53 (d, J=8.5 Hz, 2, ArH), 8.17 (dd, J=1.2, 8.5 Hz, 2, ArH), 8.91 (d, J=1.2 Hz, 2, ArH), 9.02 (s, 1, ArH), 9.43 (br.s, 2, NH).

Example 22

Synthesis of 2,10-Dicarbethoxy-6-Methoxy-5,7-dihydro-indolo[2,3-b]carbazole (74)

(a) 2,10-Dibromo-6-hydroxy-5,7-diBOC-indolo[2,3-b]carbazole (71). To a solution of 2,2,6,6-tetramethylpiperidine (7.72 g, 54.7 mmol) in THF (180 mL) at −78° C. under argon was added 1.6 M n-BuLi (49.7 mmol) in hexane (31 mL), and warmed to 0° C. for 15 min. After the reaction mixture was recooled to −78° C., 17 (3 g, 4.97 mmol) in THF (20 mL) was added slowly, and stirring was continued for 30 min before ClCO$_2$CH$_2$CH$_3$ (15 mL) was added. After 30 min, CH$_3$CO$_2$H (10 mL) in THF (10 mL) was added to the mixture at −78° C. and stirred for 10 min. The reaction mixture was poured into H$_2$O and the organic layer was washed with water; brine and concentrated to give a solid. Recrystallization (ethyl acetate/hexane) afforded 71 as a white solid (2.9 g, 92%): $^1$H NMR (300 MHz, CDCl$_3$) δ 1.74 (s, 18, OC(CH$_3$)$_3$), 7.54 (dd, J=2.0, 8.8 Hz, 2, ArH), 7.92 (d, J=8.8 Hz, 2, ArH), 7.97 (s, 1, ArH), 8.12 (d, J=2.0 Hz, 2, ArH), 11.21 (s, 1, OH).

(b) 2,10-Dibromo-6-methoxy-5,7-diBOC-indolo[2,3-b]carbazole (72). To a suspension of phenol 71 (2.3 g, 3.65 mmol) in DMF/THF (20/20 mL) at room temperature under argon was added CH$_3$I (1.1 mL, 17.7 mmol) and excess amount of K$_2$CO$_3$, and stirred for overnight. The reaction mixture was diluted with 20% EtOAc/hexane and washed with water (4 times) and brine. The combined organic extracts were dried (MgSO$_4$), filtered, and concentrated to afford a crude product. Flash chromatography (3% EtOAc/hexane) yielded 72 as a white solid (1.04 g, 91%): $^1$H NMR (300 MHz, CDCl$_3$) δ 1.75 (s, 18, OC(CH$_3$)$_3$), 3.79 (s, 3, OCH$_3$), 7.55 (dd, J=2.0, 8.8 Hz, 2, ArH), 7.97 (d, J=8.8 Hz, 2, ArH), 8.14 (d, J=2.0 Hz, 2, ArH), 8.16 (s, 1, ArH).

(c) 2,10-Dicarbethoxy-6-methoxy-5,7-diBOC-indolo[2,3-b]carbazole (73). The general procedure (b) was used to prepare 73 from 72 (2.3 g, 3.57 mmol), 1.7 M t-BuLi in pentane (10.5 mL, 17.8 mmol), and ClCO$_2$CH$_2$CH$_3$ (15 mL). Flash chromatography (10% EtOAc/hexane) yielded 73 as a white solid (2.1 g, 93%): $^1$H NMR (300 MHz, CDCl$_3$) δ 1.49 (t, J=7.0 Hz, 6, CO$_2$CH$_2$CH$_3$), 1.75 (s, 18, OC(CH$_3$)$_3$), 3.81 (s, 3, OCH$_3$), 4.47 (q, J=7.0 Hz, 4, CO$_2$CH$_2$CH$_3$), 8.11 (d, J=8.8 Hz, 2, ArH), 8.19 (dd, J=1.8, 8.8 Hz, 2, ArH), 8.40 (s, 1, ArH), 8.77 (d, J=1.8 Hz, 2, ArH).

(d) 2,10-Dicarbethoxy-6-methoxy-5,7-dihydro-indolo[2,3-b]carbazole (74). 73 (2.1 g, 3.33 mmol) was deprotected using the general procedure. Recrystallization (ethyl acetate/hexane) afforded 74 as a white solid (1.4 g, 97%): $^1$H NMR (300 MHz, CDCl$_3$) δ 1.49 (t, J=7.0 Hz, 6, CO$_2$CH$_2$CH$_3$), 4.19 (s, 3, OCH$_3$), 4.47 (q, J=7.0 Hz, 4, CO$_2$CH$_2$CH$_3$), 7.47 (d, J=8.8 Hz, 2, ArH), 8.16 (dd, J=1.8, 8.8 Hz, 2, ArH), 8.37 (br.s, 2, NH), 8.62 (s, 1, ArH), 8.90 (d, J=1.8 Hz, 2, ArH).

Example 23

Synthesis of 2-(2-Carbethoxy-indol-3-ylmethyl)-2'-carbethoxy-3,3'-diindolylmethane (75)

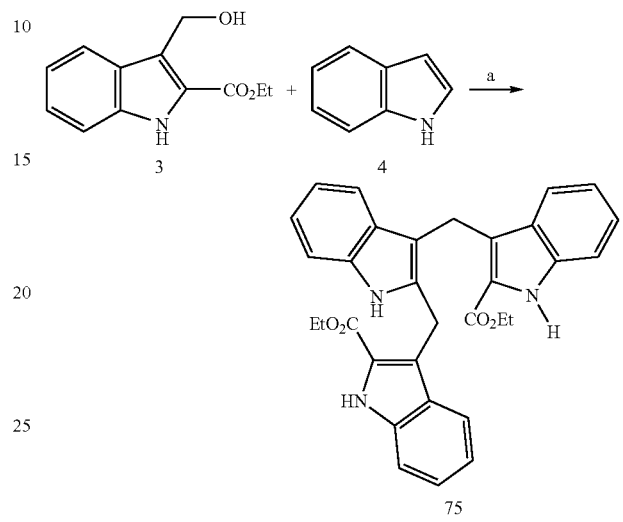

a. (CF$_3$SO$_3$)$_3$Sc.

2-(2-Carbethoxy-indol-3-ylmethyl)-2'-carbethoxy-3,3'-diindolylmethane (75). To a mixture of ethyl 3-hydroxymethyl-indole-2-carboxylate (3) (0.3 g, 1.37 mmol) and indole (4) (0.08 g, 0.68 mmol) in CH$_2$Cl$_2$ (6 mL) was added (CF$_3$SO$_3$)$_3$Sc (0.05 g) and stirred for overnight under argon. The solvent was evaporated to give a crude product. Flash chromatography (30% EtOAc/hexane) yielded 75 as a white solid (0.28 g, 79%): $^1$H NMR (300 MHz, CDCl$_3$) δ 1.40 (m, 6, CO$_2$CH$_2$CH$_3$), 4.46 (m, 4, CO$_2$CH$_2$CH$_3$), 4.61 (s, 2, CH$_2$), 4.88 (s, 2, CH$_2$), 6.86 (m, 1, ArH), 6.95 (m, 2, ArH), 7.01 (m, 1, ArH), 7.15 (m, 1, ArH), 7.25 (m, 3, ArH), 7.36 (m, 3, ArH), 7.45 (m, 1, ArH), 8.30 (br.s, 1, NH), 8.74 (br.s, 2, NH).

Example 24

Synthesis of 2-(5-carbethoxy-indol-3-ylmethyl)-5,5'-dicarbethoxy-3,3'-diindolylmethane (79)

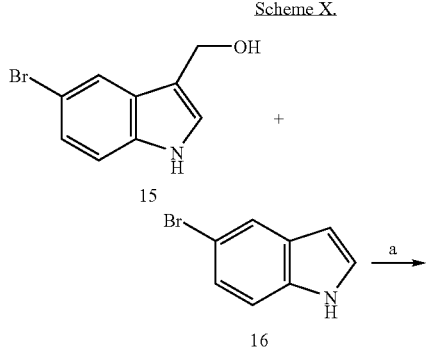

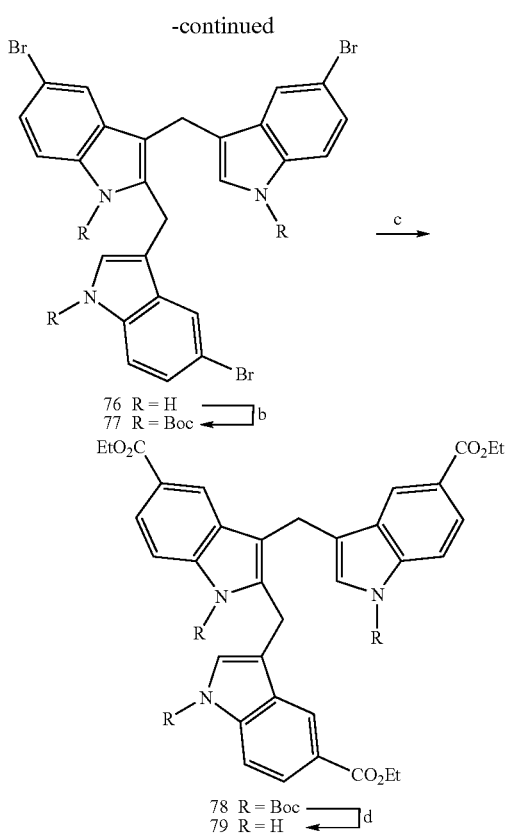

76 R = H
77 R = Boc

78 R = Boc
79 R = H a. (CF$_3$SO$_3$)$_3$Sc.
b. (t-BuOCO)$_2$O, DMAP.
c. t-BuLi; ClCO$_2$CH$_2$CH$_3$.
d. CF$_3$CO$_2$H.

(a) 1,1'-DiBOC-2-(1-BOC-5-carbethoxy-indol-3-ylmethyl)-5,5'-dibromo-3,3'-diindolylmethane (77). To a mixture of 5-bromoindole-3-carbinol (15) (7.76 g, 34.34 mmol) and 5-bromoindole (16) (6.73 g, 34.34 mmol) in CH$_2$Cl$_2$ (65 mL) was added (CF$_3$SO$_3$)$_3$Sc (1.0 g, 2.03 mmol) and stirred overnight under argon. The solvent was evaporated to give a crude product. Flash chromatography (20% EtOAc/hexane) yielded trimer 76 (1.59 g, 7.6%). To a solution of 76 (1.59 g, 2.6 mmol) and (t-BuOOC)$_2$O (1.9 g, 8.6 mmol) in THF (45 mL) was added a catalytic amount of DMAP and stirred overnight under argon. The solvent was evaporated to give a crude product. Flash chromatography (5% EtOAc/hexane) yielded 77 as a white solid (2.25 g, 95%): $^1$H NMR (300 MHz, CDCl$_3$) δ1.50 (s, 9, OC(CH$_3$)$_3$), 1.58 (s, 18, OC(CH$_3$)$_3$), 4.00 (s, 2, CH$_2$), 4.39 (s, 2, CH$_2$), 6.98 (s, 1, PyH), 7.01 (s, 1, PyH), 7.37 (m, 3, ArH), 7.55 (d, J=1.9 Hz, 2, ArH), 7.60 (d, J=1.5 Hz, 1, ArH), 7.91 (m, 2, ArH), 8.03 (d, J=9.0 Hz, 1, ArH).

(b) 1,1'-DiBOC-2-(1-BOC-5-carbethoxy-indol-3-ylmethyl)-5,5'-dicarbethoxy-3,3'-diindolylmethane (78). The general procedure (b) was used to prepare 78 from 77 (2.25 g, 2.46 mmol), 1.7 M t-BuLi in pentane (8.8 mL, 15 mmol), and ClCO$_2$CH$_2$CH$_3$ (2 mL). Flash chromatography (15% EtOAc/hexane) yielded 78 as a white solid (1.89 g, 86%): $^1$H NMR (300 MHz, CDCl$_3$) δ 1.37 (m, 9, CO$_2$CH$_2$CH$_3$), 1.48 (s, 9, OC(CH$_3$)$_3$), 1.58 (s, 9, OC(CH$_3$)$_3$), 1.59 (s, 9, OC(CH$_3$)$_3$), 4.20 (s, 2, CH$_2$), 4.35 (m, 6, CO$_2$CH$_2$CH$_3$), 4.50 (s, 2, CH$_2$), 7.02 (s, 2, PyH), 8.03 (m, 5, ArH), 8.20 (m, 4, ArH).

(c) 2-(5-Carbethoxy-indol-3-ylmethyl)-5,5'-dicarbethoxy-3,3'-diindolylmethane (79). 78 (1.8 g, 2.01 mmol) was deprotected using the general procedure. Flash chromatography (60% EtOAc/hexane) yielded 79 as a white solid (1.12 g, 94%): $^1$H NMR (300 MHz, CDCl$_3$) δ 1.37 (m, 9, CO$_2$CH$_2$CH$_3$), 4.33 (m, 10, CH$_2$, CO$_2$CH$_2$CH$_3$), 6.84 (s, 1, PyH), 7.02 (s, 1, PyH), 7.19 (d, J=8.5 Hz, 1, ArH), 7.34 (d, J=8.6 Hz, 1, ArH), 7.35 (d, J=8.6 Hz, 1, ArH), 7.81 (dd, J=1.6, 8.5 Hz, 1, ArH), 7.90 (m, 2, ArH), 7.96 (br.s, 1, NH), 8.21 (s, 1, ArH), 8.23 (s, 2, ArH), 8.27 (br.s, 1, NH), 8.45 (br.s, 1, NH).

Example 25

In Vitro Determination of Growth Inhibitory, Estrogenic, and Antiestrogenic Activities of DIM, LT, and Novel Analogs in Breast Cancer Cell Lines Growth inhibition assays were conducted using DIM, LT, and some of the novel compounds of the invention on several breast cancer cell lines. The cell lines studied were MCF-7 (ER$^+$), MDA-MB-231 (ER$^-$), and a tamoxifen-resistant strain of MCF-7 (ER$^+$). The growth assays were conducted according to the method of Tiwari et al. (Tiwari, R. K., J Natl Cancer Inst 86:126-131, 1994). For growth Inhibition Assay, cells were grown in multi-well culture plates. Experiments were performed in quadruplicate. MCF-7 (ER$^+$) cells were grown in special medium containing 5% animal serum that had been treated to remove endogenous estrogens. After the plates were incubated at 37° C. for 24 hours, to each well was added test compound at various concentrations, with or without the estrogen 17β-estradiol (E$_2$). The cells were then incubated for 7 days, with medium and test solutions replaced every other day. On Day 8, after the medium was removed and replaced with fresh medium without test solutions, the tetrazolium blue test was performed to determine the percentage of viable cells (viable cells convert the colorless tetrazolium to formazan, which is blue). At 4 hours after tetrazolium blue was added, the reaction was stopped and the formazan concentration was measured by detection of light absorbance at 575 nm in an enzyme linked immunosorbent assay (ELISA) plate reader. The percent growth inhibition was determined by dividing the ELISA results for samples containing test compounds by the results for control samples. MDA-MB-321 (ER$^-$) cells were maintained and tested under the same conditions as described above, except that no estrogen was added.

Estrogenic and antiestrogenic activities were determined using the Ishikawa assay (Littlefield, B. A., Endocrinology 127: 2757-2762, 1990). The activities were measured at 10 μM concentrations of the test compounds. Human Ishikawa cells (endometrial carcinoma cells) are very sensitive to estrogens, and compounds with estrogenic activity induce alkaline phosphatase (AlkP) enzyme activity in these cells when administered at levels as low as 10$^{-12}$ M. Ishikawa cells were grown in growth medium supplemented with glutamine, sodium pyruvate, and 10% animal serum. At 24 hours before the experiment, the medium was replaced with medium free of phenol red and containing 5% animal serum that had been treated to remove endogenous estrogens. On Day 1, the cells were harvested and plated in fresh phenol red-free medium, and test solutions were added with or without the estrogen 17β-estradiol. After the treated cells were incubated for 72 hours, the AlkP assay was used to determine the estrogenic and antiestrogenic activity of the test compounds. Like the tetrazolium blue assay described above, this assay involves calorimetric detection using an ELISA plate reader, but here the indicator dye is yellow.

Results of these studies for some of the compounds are presented in Table 1. These compounds displayed potent growth inhibition of all three breast cancer cell lines studied, including estrogen-dependent, estrogen-independent and the drug-resistant cell lines. Growth inhibition was considerably greater for the novel compounds than for DIM or LT, which are themselves considerably more potent than I3C. In addition, the novel compounds all displayed strong antiestrogenic activity with no measurable estrogenic activity. DIM, by contrast, displayed moderate estrogenic and antiestrogenic activities in the Ishikawa assay.

TABLE 1

Growth inhibitory, antiestrogenic, and estrogenic activities of I3C metabolites and novel compounds.

| | Breast Cancer Cell Lines | | | | Ishikawa Cells | |
|---|---|---|---|---|---|---|
| | MCF-7 | | MDA-MB-231 | | Tamoxifen- | Ishikawa Assay |
| | (ER+) | | (ER−) | | resistant | Anti- |
| Compound | $IC_{50}$ ($\mu M$) | % Growth Inhibition at 1 $\mu M$ | $IC_{50}$ ($\mu M$) | % Growth Inhibition at 10 $\mu M$ | MCF-7 $IC_{50}$ ($\mu M$) | Estrogenic Activity at 10 $\mu M$ | Estrogenic Activity at 10 $\mu M$ |
| DIM | 5.5 | 3 | 31 | 20 | >10 | 52 | 30 |
| LT | 1.8 | 19 | 13 | 34 | 0.6 | 0 | 100 |
| 46 | 0.031 | 100 | 6.9 | 81 | 0.46 | 0 | 94 |
| 58 | 0.018 | 100 | 2.1 | 97 | 0.056 | 0 | 100 |
| 63 | 1.4 | 66 | 2.0 | 94 | 3.0 | 0 | 100 |
| 74 | 0.2 | 100 | 7.8 | 69 | 0.93 | 0 | 80 |

Example 26

In Vitro Determination of Growth Inhibitory Activity of Compound 74 on Ovarian Cancer Cell Lines Assays were conducted on compound 74 (SR13668) to determine its growth inhibitory effect on two ovarian cancer cell lines, NIH-OVCAR-3 and SKOV-3. OVCAR-3 cells are routinely maintained in RPMI-1640 medium supplemented with 2 mM glutamine (GLN) and 10% fetal calf serum (FCS), and SKOV-3 cells in McCoy's 5A medium supplemented with 2 mM GLN and 10% FCS. Both cell lines are fed with fresh medium every other day and passaged every 6-7 days. To conduct the growth inhibition assay, cells from either cell line are seeded in 96-well plates at 2000 cells/well in 200 µL of medium. After cells are allowed to attach for 24 h, test compounds dissolved in dimethyl sulfoxide (DMSO) and further diluted with medium are added to each well in 10-µL aliquots. The final DMSO concentration is kept at 0.05%. Control wells receive vehicle only. Media and test solutions are replaced every other day. On Day 7, viable cells are measured with the MTT (tetrazolium blue) assay, using an MTT kit.

Compound 74 was found to be potent at inhibiting the growth of cells from both lines: the $IC_{50}$ values were 5.1 µM for NIH-OVCAR-3 and 4.0 µM for SKOV-3. As both of these cell lines are cisplatin-resistant and represent aggressive, difficult to treat cancers, these results are highly encouraging and indicate a potential breakthrough in the treatment of ovarian cancer.

Example 27

In Vitro Determination of Growth Inhibitory Activity of 46 on Prostate Cancer Cell Lines Assays were conducted on compound 46 (SR13654) to determine its growth inhibitory effect on three prostate cancer cell lines, LNCaP, DU-145 and PC-3. The methods were described briefly herein. LNCaP and PC-3 cells will be maintained in RPMI-164 medium, and DU-145 cells in Eaglets minimal essential medium (MEM) medium supplemented with nonessential amino acids, 2 mM glutamine and 1 mM pyruvate. All media will contain 10% fetal bovine serum (FCS). To screen compounds for their effect on cell proliferation, cells are seeded in 96-well plates at 2000 cells/well in 200 µL of medium. After cells are allowed to attach for 24 h, test compound is added to each well in 10 µL aliquots and control wells receive vehicle only. Medium and test solutions are replaced every other day. On Day 7, viable cells are measured with the MTT assay, using the protocol provided by the manufacturer (Promega, Madison, Wis.).

Compound 46 showed potent growth inhibitory activity in these three cell lines: the $IC_{50}$ values were 4.7 µM for LNCaP, 0.48 µM for DU-145 and 0.2 µM for PC-3. As DU-145 and PC-3 are invasive and androgen-nonresponsive cell lines, which have highly metastatic potential and can not be treated by antiandrogen, these results are very promising and indicate a potential breakthrough in the treatment of prostate cancer.

Example 28

In Vitro Determination of Anti-Invasive Activity of Compound 74 on (ER−) MDA-MB-231 Breast Cancer Cell Lines In in vitro invasion studies, it is very important to demonstrate that inhibition of invasion is not due to cell killing or simple cell growth inhibition; thus, we also conducted parallel cell growth inhibition assays in these studies. MDA-MB-231 human carcinoma cells was used for this Boyden Chamber Invasion Assay (Meng et al. (2000) J. Mol. Med. 78, 155-165; Meng et al. (2000) Breast Cancer Res. Treat. 63, 147-152). Briefly, to each well of a 24-well Biocoat invasion chamber plate, 0.6 mL of appropriate medium containing 10% FCSH 6 µg/ml Fibronectin is added, followed by gentle placement of a CCI in each well. To each CCI is added freshly harvested cells suspended in 200 µL of medium containing either the test compound or vehicle alone. The preparations are incubated at 37° C. for 16 h, and then the CCI is removed from each well, fixed for 10 min with 1 ml of 3.7% paraformaldehyde in PBS, and stained for 10 min in 1 mL of Wright-Giemsa stain solution. The stained CCI is placed on a glass microscope slide and the upper surface cells are carefully removed by scraping with a cotton swab. The cells on the lower surface are counted in a bright field microscope. The inhibitory effect of a test compound is calculated by dividing the number of cells in a treated preparation by that of the vehicle control and expressed as a percentage.

Results of these studies show that compound 74 only exhibited 22% growth inhibition at 5 μM concentration, while compound 74 exhibited a 90% reduction in the invasive capacity of MDA-MB-231 cells at the same concentration, with an identical 16 h end-point. As invasion leads to metastasis, and metastases turn cancer into an incurable disease, any promising new strategy or therapeutic with curative intent should aim not only at cell proliferation but also at cell invasion to achieve a cumulative benefit in cancer therapy. These results indicate these novel indole analogs have potential in the suppression of cancer metastasis.

Example 29

Antitumorigenic Activity of Orally Administered Compound 74 Against ER+ MCF-7 Breast Cancer Xenografts in Nude Mice To study the in vivo activity of novel compound 74 against estrogen-dependent breast cancer, the compound was administered to nude mice that had been implanted with (ER) MCF-7 breast cancer cells. To start the experiment, female Balb/c nude mice were implanted subcutaneously (s.c.) with estrogen pellets two days prior to inoculation of cancer cells, for stimulation of cell growth. MCF-7 cells were then implanted s.c. in the flanks, using an inoculum of 5×10$^6$ cells in a medium-Matrigel mixture (1:1, v/v). When the mean tumor volume reached approximately 100 mm$^3$, the test compound in 0.5% hydroxypropylcellulose in sterile saline solution (or vehicle alone for controls) was administered orally by gavage daily. There were 7 mice in the experimental and control groups. Mice were examined daily for tumor growth, and tumors and body weight were measured twice weekly. The tumor volume is $4/3\pi r_1^2 r_2$, where $r_1$ and $r_2$ are the short radius and long radius, respectively. On Day 27, all the mice were sacrificed, and the major organs examined by a pathologist.

As shown in FIG. 1, mice that received compound 74 consistently had tumor volumes that were less than half of those in the control mice, which did not receive compound 74. The body weights of the treated mice were unaffected, indicating that compound 74 has no adverse effect.

Example 30

Antitumorigenic Activity of Orally Administered 74 on (ER−) MDA-MB-231 Breast Cancer Xenografts in Nude Mice As a further test of in vivo efficacy against estrogen-independent breast cancer, the novel compound 74 was administered to nude mice that had been implanted with (ER−) MDA-MB-231 human breast cancer xenografts. To start, female Balb/c nude mice were implanted subcutaneously (s.c.) with MDA-MB-231 cells, using an inoculum of 5×10$^6$ cells in a medium-Matrigel mixture (1:1, v/v). When the mean tumor volume reached approximately 70 mm$^3$, compound was administered daily at three dose levels (10, 30, and 100 mg/kg) via oral gavage. The methods used in the study were essentially the similar to those described in Example 29 herein.

Figure 2:
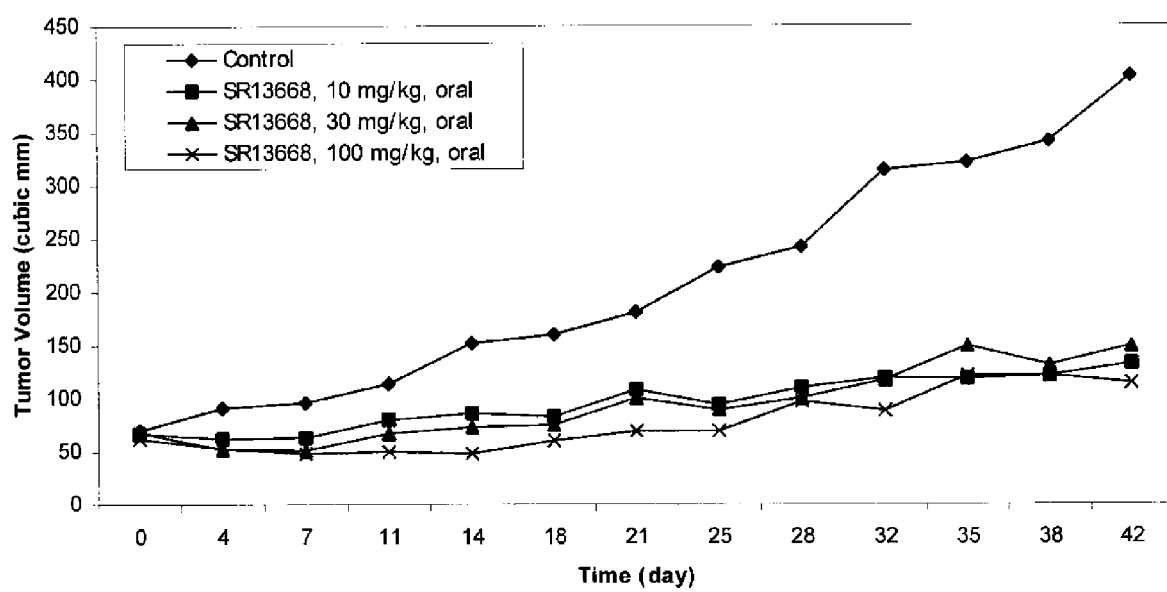
FIG. 2 is a graph illustrating the antitumorigenic activity of the same compound against ($ER^-$) MDA-MB-231 breast cancer xenografts in nude mice, as evaluated in Example 30.

As shown in FIG. 2, mice that received compound 74 consistently had tumor volumes that were less than half of those in the control mice, which did not receive compound 74. The body weights of the treated mice were unaffected, indicating that compound 74 had no adverse effect.

Example 31

Figure 3:
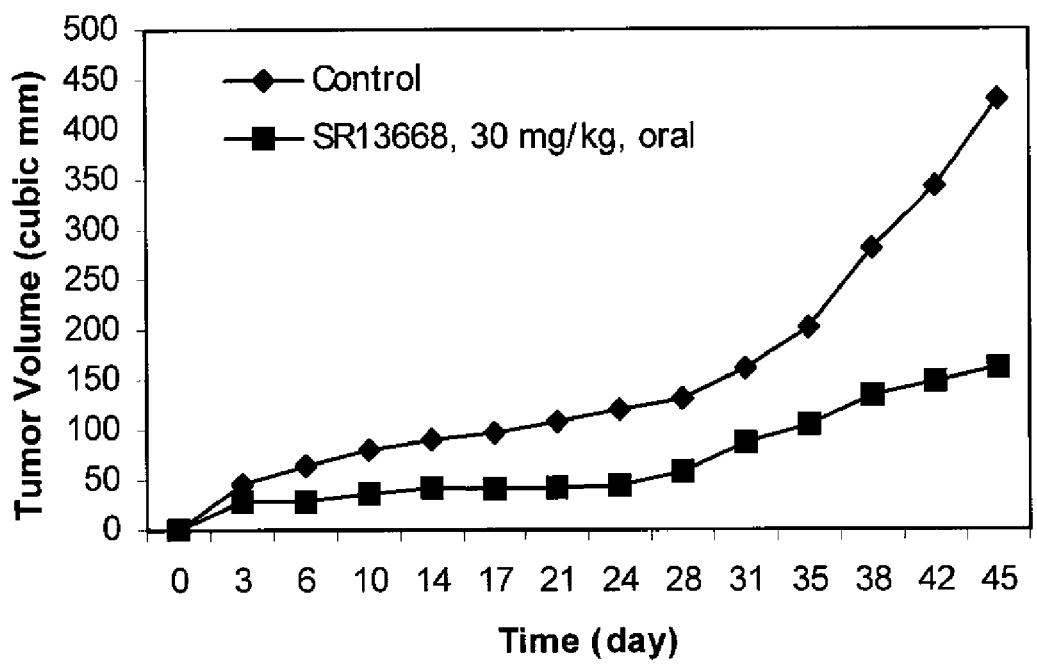
FIG. 3 is a graph illustrating the antitumorigenic activity of the same compound on SKOV-3 human ovarian cancer xenografts in nude mice, as evaluated in Example 31.

Antitumorigenic Activity of Orally Administered 74 on SKOV-3 Human Ovarian Cancer Xenografts in Nude Mice To start, female Balb/c nude mice were implanted subcutaneously (s.c.) with SKOV-3 cells in the flanks, using an inoculum of 5×10$^6$ cells in a medium-Matrigel mixture (1:1, v/v), and compound 74 (30 mg/kg) was orally administered daily via gavage from Day 0. Tumor volume and body weight were measured twice weekly. The body weights of the treated mice were unaffected, indicating that compound 74 has low systemic toxicity. As shown in FIG. 3, mice that received compound 74 consistently had tumor volumes that were significantly less than those in the control mice, which did not receive compound 74. Since SKOV-3 is a highly drug-resistant human ovarian cancer cell line and represent aggressive, difficult to treat cancers, these results are highly encouraging and indicate a potential breakthrough in the treatment of ovarian cancer.

We claim:
1. A compound having the structure of formula (IV)

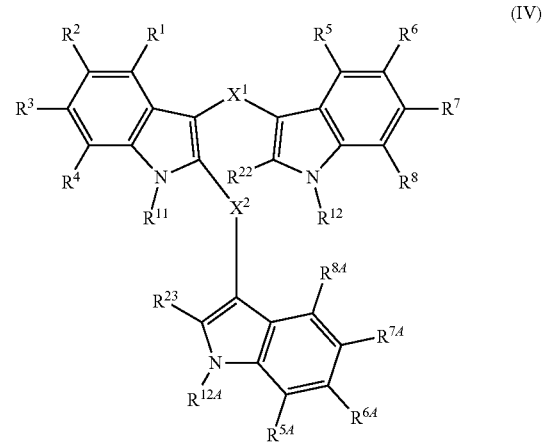

wherein:
$R^1$, $R^2$, $R^3$, $R^4$, $R^5$, $R^6$, $R^7$, $R^8$, $R^{5A}$, $R^{6A}$, $R^{7A}$, $R^{8A}$, $R^{22}$ and $R^{23}$ are independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$aryl)-substituted amino, $C_2$-$C_{24}$alkylamido, $C_5$-$C_{20}$arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms;

$R^{11}$, $R^{12}$, and $R^{12A}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl)amino-substituted $C_1$-$C_{24}$ alkyl; and $X^1$ and $X^2$ are independent selected from O, S, arylene, heteroarylene, $CR^{15}R^{16}$ and $NR^{17}$ wherein $R^{15}$ and $R^{16}$ are hydrogen, $C_1$-$C_6$ alkyl, or together form $=CR^{18}R^{19}$ where $R^{18}$ and $R^{19}$ are hydrogen or $C_1$-$C_6$ alkyl, and $R^{17}$ is as defined for $R^{11}$ and $R^{12}$, with the proviso that at least one of $R^1$, $R^2$, $R^3$, $R^4$, $R^5$, $R^6$, $R^7$, $R^8$, $R^{5A}$, $R^{6A}$, $R^{7A}$, $R^{8A}$, $R^{22}$ and $R^{23}$ is other than hydrogen.

2. The compound of claim 1, wherein $R^1$, $R^3$, $R^4$, $R^5$, $R^7$, $R^8$, $R^{5A}$, $R^{7A}$, and $R^{8A}$ are hydrogen, and $X^1$ and $X^2$ are $CH_2$, such that the compound has the structure of formula (IVa)

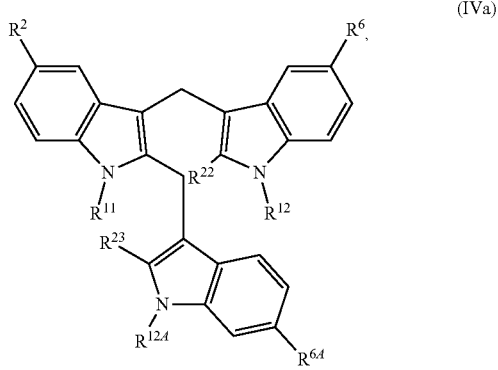

(IVa)

with the proviso that at least one of $R^2$, $R^6$, $R^{6A}$, $R^{12}$, $R^{12A}$, $R^{22}$ and $R^{23}$ is other than hydrogen.

3. The compound of claim 2, wherein $R^2$, $R^6$, $R^{6A}$, $R^{22}$, and $R^{23}$ are independently selected from the group consisting of halo, $C_1$-$C_{12}$ alkyl, $C_1$-$C_{12}$ alkoxy, $C_2$-$C_{12}$ alkoxycarbonyl, $C_2$-$C_{12}$ alkylcarbonato, carbamoyl, mono-($C_1$-$C_{12}$ alkyl)-substituted carbamoyl, di-($C_1$-$C_{12}$ alkyl)-substituted carbamoyl, $C_1$-$C_{12}$ alkylsulfanyl, $C_1$-$C_{12}$ alkylsulfinyl, and $C_1$-$C_{12}$ alkylsulfonyl.

4. The compound of claim 3, wherein at least one of $R^2$, $R^6$, $R^{6A}$, $R^{22}$, and $R^{23}$ is $C_2$-$C_{12}$ alkoxycarbonyl or $C_2$-$C_{12}$ alkylcarbonato.

5. The compound of claim 2, wherein $R^{11}$, $R^{12}$, and $R^{12A}$ are independently selected from the group consisting of hydrogen, $C_1$-$C_{12}$ alkyl, $C_2$-$C_{12}$ alkoxycarbonyl, amino-substituted $C_1$-$C_{12}$ alkyl, ($C_1$-$C_{12}$ alkylamino)-substituted $C_1$-$C_{12}$ alkyl, and di-($C_1$-$C_{12}$ alkyl)amino-substituted $C_1$-$C_{12}$ alkyl.

6. The compound of claim 2, wherein:
$R^2$, $R^6$, $R^{6A}$, $R^{22}$, and $R^{23}$ are independently selected from hydrogen and $C_2$-$C_6$ alkoxycarbonyl; and
$R^{11}$, $R^{12}$, and $R^{12A}$ are independently selected from hydrogen and $C_1$-$C_6$ alkyl.

7. The compound of claim 6, wherein:
$R^2$, $R^6$, $R^{6A}$, $R^{22}$, and $R^{23}$ are independently selected from hydrogen and ethoxycarbonyl;
$R^{11}$, $R^{12}$, and $R^{12A}$ are hydrogen.

8. The compound of claim 7, wherein at least one of $R^2$, $R^6$, $R^{6A}$, $R^{22}$, and $R^{23}$ is ethoxycarbonyl.

9. A pharmaceutical composition comprising the compound of claim 1 in combination with a pharmaceutically acceptable carrier.

10. The composition of claim 9, wherein the pharmaceutically acceptable carrier is suitable for oral administration and the composition comprises an oral dosage form.

11. The composition of claim 10, wherein the oral dosage form is a tablet or a capsule.

12. The composition of claim 9, wherein the pharmaceutically acceptable carrier is suitable for parenteral administration and the composition comprises a parenterally administrable formulation.

13. A method for treating cancer selected from the group consisting of breast, cervix, uterus, ovaries, endometrium, prostate, and lung cancer in a mammalian individual, comprising administering to the individual a therapeutically effective amount of the compound of claim 1.

14. The method of claim 13, wherein the cancer is of the breast, cervix, uterus, ovaries, or endometrium.

15. The method of claim 14, wherein the cancer is metastasized.

16. The method of claim 14, wherein the cancer is a drug-resistant cancer.

17. The method of claim 16, wherein the cancer exhibits multiple drug resistance.

18. The method of claim 13, wherein the cancer is of the prostate or lung.

19. The method of claim 18, wherein the cancer is metastasized.

20. The method of claim 18, wherein the cancer is a drug-resistant cancer.

21. The method of claim 20, wherein the cancer exhibits multiple drug resistance.

22. A method for treating a viral infection, comprising administering an the individual a therapeutically effective amount of the compound of claim 1.

23. The method of claim 22, wherein the viral infection is caused by a DNA virus.

24. The method of claim 23, wherein the DNA virus is human papillomavirus.

25. The method of claim 23, wherein the viral infection is a retroviral infection.

* * * * *